US006908737B2

(12) United States Patent

Ravkin et al.

(10) Patent No.: US 6,908,737 B2

(45) Date of Patent: *Jun. 21, 2005

(54) SYSTEMS AND METHODS OF CONDUCTING MULTIPLEXED EXPERIMENTS

(75) Inventors: Ilya Ravkin, Palo Alto, CA (US); Simon Goldbard, San Jose, CA (US); William C. Hyun, San Francisco, CA (US); Michael A. Zarowitz, San Carlos, CA (US)

(73) Assignee: Vitra Bioscience, Inc., Mountain View, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 10/119,814

(22) Filed: Apr. 9, 2002

(65) Prior Publication Data

US 2003/0008323 A1 Jan. 9, 2003

Related U.S. Application Data

(60) Division of application No. 09/694,077, filed on Oct. 19, 2000, now abandoned, and a continuation-in-part of application No. 09/692,526, filed on Oct. 18, 2000, which is a continuation-in-part of application No. 09/549,970, filed on Apr. 14, 2000.

(60) Provisional application No. 60/241,714, filed on Oct. 18, 2000, provisional application No. 60/170,947, filed on Dec. 15, 1999, and provisional application No. 60/129,664, filed on Apr. 15, 1999.

(51) Int. Cl.[7] .................................................. C12Q 1/68

(52) U.S. Cl. ............................ 435/6; 435/7.1; 435/7.2; 435/808; 435/968; 422/68.1; 422/82.05; 422/82.08; 422/82.09; 436/807

(58) Field of Search ............................. 435/6, 7.1, 7.2, 435/808, 968; 422/68.1, 82.05, 82.08, 82.09; 436/807

(56) References Cited

U.S. PATENT DOCUMENTS

| | | | |
|---|---|---|---|
| 3,772,099 A | | 11/1973 | Ryan et al. |
| 3,897,284 A | | 7/1975 | Livesay |
| 3,964,294 A | | 6/1976 | Shair et al. |
| 4,053,433 A | * | 10/1977 | Lee ......................... 252/408.1 |
| 4,131,064 A | | 12/1978 | Ryan et al. |
| 4,197,104 A | | 4/1980 | Krystyniak et al. |
| 4,329,393 A | | 5/1982 | LaPerre et al. |
| 4,363,965 A | | 12/1982 | Soberman et al. |
| 4,469,623 A | | 9/1984 | Danielson et al. |
| 4,640,035 A | | 2/1987 | Kind et al. |
| 4,652,395 A | | 3/1987 | Marcina et al. |
| 5,143,854 A | | 9/1992 | Pirrung et al. |
| 5,202,265 A | | 4/1993 | LaMora |
| 5,409,839 A | | 4/1995 | Balestrieri |
| 5,451,505 A | | 9/1995 | Dollinger |
| 5,563,583 A | | 10/1996 | Brady et al. |
| 5,581,257 A | | 12/1996 | Greene et al. |
| 5,688,696 A | | 11/1997 | Lebl |
| 5,708,153 A | | 1/1998 | Dower et al. |
| 5,741,462 A | | 4/1998 | Nova et al. |
| 5,744,305 A | | 4/1998 | Fodor et al. |
| 5,751,629 A | | 5/1998 | Nova et al. |
| 5,760,394 A | | 6/1998 | Welle |
| 5,770,455 A | | 6/1998 | Cargill et al. |
| 5,786,626 A | | 7/1998 | Brady et al. |
| 5,817,751 A | | 10/1998 | Szardenings et al. |

(Continued)

FOREIGN PATENT DOCUMENTS

| | | |
|---|---|---|
| GB | 2 306 484 | 7/1997 |
| WO | 96/36436 | 11/1996 |
| WO | WO 97/12680 | 4/1997 |
| WO | WO 97/20074 | 6/1997 |
| WO | WO9735201 | 9/1997 |
| WO | 98/46550 | 10/1998 |
| WO | 98/53093 | 11/1998 |
| WO | WO9919515 | 4/1999 |
| WO | WO9922018 | 5/1999 |
| WO | WO9936564 | 7/1999 |
| WO | WO9937814 | 7/1999 |
| WO | WO9941006 | 8/1999 |
| WO | WO9967641 | 12/1999 |
| WO | WO0000145 | 1/2000 |
| WO | WO0022435 | 4/2000 |
| WO | WO0032542 | 6/2000 |
| WO | WO0033079 | 6/2000 |
| WO | WO0039587 | 6/2000 |
| WO | WO0073777 | 12/2000 |
| WO | WO 01/25002 | 4/2001 |
| WO | WO0125510 | 4/2001 |
| WO | WO0161040 | 8/2001 |
| WO | WO0177391 | 10/2001 |
| WO | WO0178288 | 10/2001 |
| WO | WO0189585 | 11/2001 |
| WO | WO0196604 | 12/2001 |
| WO | WO0198765 | 12/2001 |

OTHER PUBLICATIONS

Blawas, A.S.; Reicher, W. M. "Protein Patterning" Biomaterials 1998 19, 595–609.*

*Primary Examiner*—Bennett Celsa
*Assistant Examiner*—Jon D. Epperson
(74) *Attorney, Agent, or Firm*—Kolisch Hartwell, P.C.

(57) ABSTRACT

A method for multiplexed detection and quantification of analytes by reacting them with probe molecules attached to specific and identifiable carriers. These carriers can be of different size, shape, color, and composition. Different probe molecules are attached to different types of carriers prior to analysis. After the reaction takes place, the carriers can be automatically analyzed. This invention obviates cumbersome instruments used for the deposition of probe molecules in geometrically defined arrays. In the present invention, the analytes are identified by their association with the defined carrier, and not (or not only) by their position. Moreover, the use of carriers provides a more homogenous and reproducible representation for probe molecules and reaction products than two-dimensional imprinted arrays or DNA chips.

18 Claims, 18 Drawing Sheets

U.S. PATENT DOCUMENTS

| | | | | |
|---|---|---|---|---|
| 5,840,485 | A | 11/1998 | Lebl et al. | |
| 5,846,719 | A | 12/1998 | Brenner et al. | |
| 5,874,214 | A | 2/1999 | Nova et al. | |
| 5,874,724 | A | 2/1999 | Cato | |
| 5,925,562 | A | 7/1999 | Nova et al. | |
| 5,961,923 | A | 10/1999 | Nova et al. | |
| 5,981,166 | A | 11/1999 | Mandecki | |
| 5,981,180 | A | 11/1999 | Chandler et al. | |
| 5,989,835 | A | 11/1999 | Dunlay et al. | |
| 5,990,479 | A | 11/1999 | Weiss et al. | |
| 6,017,496 | A | 1/2000 | Nova et al. | |
| 6,018,299 | A | 1/2000 | Eberhardt | |
| 6,025,129 | A | 2/2000 | Nova et al. | |
| 6,025,200 | A | 2/2000 | Kaish et al. | |
| 6,046,003 | A | 4/2000 | Mandecki | |
| 6,051,377 | A | 4/2000 | Mandecki | |
| 6,083,693 | A | 7/2000 | Nandabalan et al. | |
| 6,083,763 | A | 7/2000 | Balch | |
| 6,093,370 | A | 7/2000 | Yasuda et al. | |
| 6,100,026 | A | 8/2000 | Nova et al. | |
| 6,100,973 | A | 8/2000 | Lawandy | |
| 6,104,038 | A | 8/2000 | Gonzalez et al. | |
| 6,114,038 | A | 9/2000 | Castro et al. | |
| 6,129,896 | A | * 10/2000 | Noonan et al. | 422/82.05 |
| 6,136,274 | A | 10/2000 | Nova et al. | |
| 6,210,910 | B1 | 4/2001 | Walt et al. | |
| 6,214,560 | B1 | 4/2001 | Yguerabide et al. | |
| 6,238,869 | B1 | 5/2001 | Kris et al. | |
| 6,251,691 | B1 | 6/2001 | Seul | |
| 6,274,323 | B1 | 8/2001 | Bruchez et al. | |
| 6,296,189 | B1 | 10/2001 | Lawandy et al. | |
| 6,306,975 | B1 | 10/2001 | Zhao et al. | |

* cited by examiner 204
202
203

205
204
202
203

204
202
203

205a
205a
204
202
203

205a
204a 205
201
204

204a
205
204
202
203

804
805
803
806
807
808
805a 803
810
806
805a
807
808
805a
811
808
810
807
806
805a

SYSTEMS AND METHODS OF CONDUCTING MULTIPLEXED EXPERIMENTS

CROSS-REFERENCE TO RELATED APPLICATIONS

This application is a divisional application of U.S. application Ser. No. 09/694,077 which was filed on Oct. 19, 2000, now abandoned which is a continuation-in-part of U.S. application Ser. No. 09/549,970 filed Apr. 14, 2000; which claims the priority of U.S. Provisional Application Ser. No. 60/170,947 filed Dec. 15, 1999 and of U.S. Provisional Application Ser. No. 60/129,664 filed Apr. 15, 1999, both of which are herein incorporated in their entirety by reference. It also claims the benefit of U.S. Provisional Application Ser. No. 60/241,714 filed Oct. 18, 2000, titled "Composition and Method for Multiplexed Analysis of Cell Populations", by Ravkin, and U.S. Continuation-in-part application Ser. No. 09/692,526 filed Oct. 18, 2000, titled "Chemical-Library Composition and Method", by Ravkin, et al., both of which are herein incorporated by their entirety by reference.

FIELD OF THE INVENTION

This invention relates to a method for the multiplexed detection, analysis, and quantification of analytes.

BACKGROUND OF THE INVENTION

Multiplexed analysis of analytes is an important tool in biomedical discovery such as drug development, genome analysis, and diagnostics. An exemplary use of multiplexed analysis is the study of the human genome structure and expression. Recent study of the human genome has demanded simultaneous study of many genomic sites instead of serially studying individual sites. Particularly important to multiplexed genomic analysis are tools such as nucleic acid arrays commonly known as DNA chips.

Although the basic principles behind microarrays are sound, the manufacture and analysis is expensive and complex. As a result, while the number of potential applications is great, few laboratories can afford the technology for their diagnostic or research goals. The described invention addresses this discrepancy allowing for multiplexed analysis that will not have the cost prohibitions of current microarray products.

Arrays are also used in drug discovery, for example, by identifying gene expression of human cells and their response to drugs, hormones, inhibitors, enzymes, and other molecules. Although the basic principles behind arrays are sound, previously described methods are difficult and costly to manufacture and analysis is often expensive and complex. Signature patterns of expression may indicate new drug targets, permit rapid screening for drugs of desired effect, and potentially reduce the time from bench to bedside. One of the most important applications of microarrays will probably be in the field of pharmacogenetics. Pharmacogenetics is the study of how an individual's genetics can affect the probability of different treatment outcomes and how the response to a medication can differ based on an individual's genetically determined metabolic constitution. These differences arise from polymorphisms (minor differences in gene sequences) in the genes responsible for the actual drug target or in genes that direct metabolic enzymes that activate, deactivate, or alter the drug in the body. Microarrays will be used during the drug discovery process, the screening of participants in clinical drug trials, and very likely as part of the standard clinical work up of patients.

Multiplexed analysis of analyte samples may be achieved by parallel processing. In particular, reactions where an analyte will selectively react with a sub-population compound from a larger population of different compounds, are ideally suited for parallel analysis. For example, U.S. Pat. No. 5,744,305, herein incorporated in its entirety by reference, describes the use of a collection of compounds arrayed on a planar surface, where particular compounds are synthesized at particular regions on the planar surface. The array is then contacted with an analyte such that certain compounds in the analyte will specifically bind an array compound.

Existing array methods require arraying compounds by situating such compounds onto surfaces, for example, a glass slide, in predefined different locations either by spotting preformed compounds, or by synthesizing compounds in-situ. Compound identity is maintained solely by its position upon the array surface. Accordingly, the entire array must remain intact for the duration of the analysis. For example, compound identity would be lost if the array were sectioned into individual compound sections that were then randomly shuffled. It is impossible, therefore, to recreate the original array without knowledge of the chemical identity of each compound section. A shuffled array may be reconstructed, however, if the chemical identity of each compound section could be ascertained. Direct analysis is unlikely since the amount of compound present within a compound section is often too minute. If a unique and detectable code is associated with each compound section, then the code would correlate to a particular compound, or region within the array, from which the compound section was derived. A coded compound section then comprises a substrate linking a compound and a code. Encoding compounds imparts portability upon the compound not found with unencoded compound arrays.

Arrays can be in the form of two-dimensionally distributed microscopic spots of nucleic acid material deposited on a solid matrix, usually a microscopy slide. The task of depositing thousands of these spots requires automation. One approach to automation is to print arrays by using computer controlled high-speed robotics. Here, pre-formed different DNA probe regions are produced by first amplifying target DNA by PCR. Next, minute samples of the now amplified DNA are transferred to glass slides using a robotic printer head. Glass slides are pre-coated with a chemical linker that will retain the probe DNA spots in place despite heat denaturation. Standardization and reproducibility of array spotting is difficult to achieve—by printing arrays because of the source of the molecules and the method for their deposition. For example, DNA can be viscous and therefore hard to deliver accurately through the narrow channels of a typical print head.

When arrays are manufactured with print heads, the print heads must first be filled with different samples of probe DNA, and then the head is moved for deposition on slides. This requires the use of computerized robotics to direct the print head to go back and forth between the source of DNA, particular coordinates on the solid matrix (glass slide), and washing and drying stations. The printing speed allows 20–60 arrays each containing 4000 compound locations to be manufactured in 3–4 hours. Scalability is accomplished by simultaneously printing more arrays. This, of course, necessitates additional expensive spotting systems, thus raising costs.

An alternative to printed arrays is the use of light-directed synthesis to construct high-density DNA probe arrays (or DNA chips). Instead of depositing DNA solutions on a slide surface, the DNA is formed in situ by synthesizing a desired DNA sequence directly onto a solid support. The solid support typically contains a covalent linker molecule with a photolabile-protecting group. By selectively applying light to some sites and not others, the light exposed sites become activated. Activated sites then react with protected nucleotides while the inactivated sites remain unaltered. This cycle can be repeated several times using different masks and thus producing a high-density two-dimensional matrix containing different sequence probes. Complex DNA mixtures are then analyzed by correlating active compounds to their fixed position within the two dimensional array.

DNA applied to array surfaces can be derived from fully or partially sequenced DNA clones, EST's (Expressed Sequence Tags), or any cDNA chosen from a library. A two-color hybridization scheme is typically used to monitor the presence or amplification of the DNA regions of interest. Two-color analysis provides for comparison of two DNA sources. For example, in CGH (Comparative Genomic Hybridization), one source of DNA is the test DNA and the other is the reference DNA. After these two fluorescently labeled sets of DNA are hybridized to the array, the resulting ratio of fluorescence intensities at a given spot can be quantified. This measurement then yields a ratio of copy number corresponding to the reference and test DNA associated with that particular DNA or probe region of the array.

Both spotted and in-situ arrays must be individually manufactured by expensive and often temperamental equipment. In-situ synthesis requires hours of stepwise reactions to create one individual compound array. Even if multiple arrays are synthesized simultaneously, the process is machine and mask limited. Moreover, each time a new array compound pattern is desired, a new set of masks must be fashioned. This problem magnifies as higher densities of different compounds are placed onto the array surface. Since compound identity information is strictly positional, highly accurate placement of individual compounds is an absolute and non-trivial requirement for fabricating high-density arrays.

The invention described herein overcomes these and other problems with present array technology.

SUMMARY OF THE INVENTION

Figure 1:
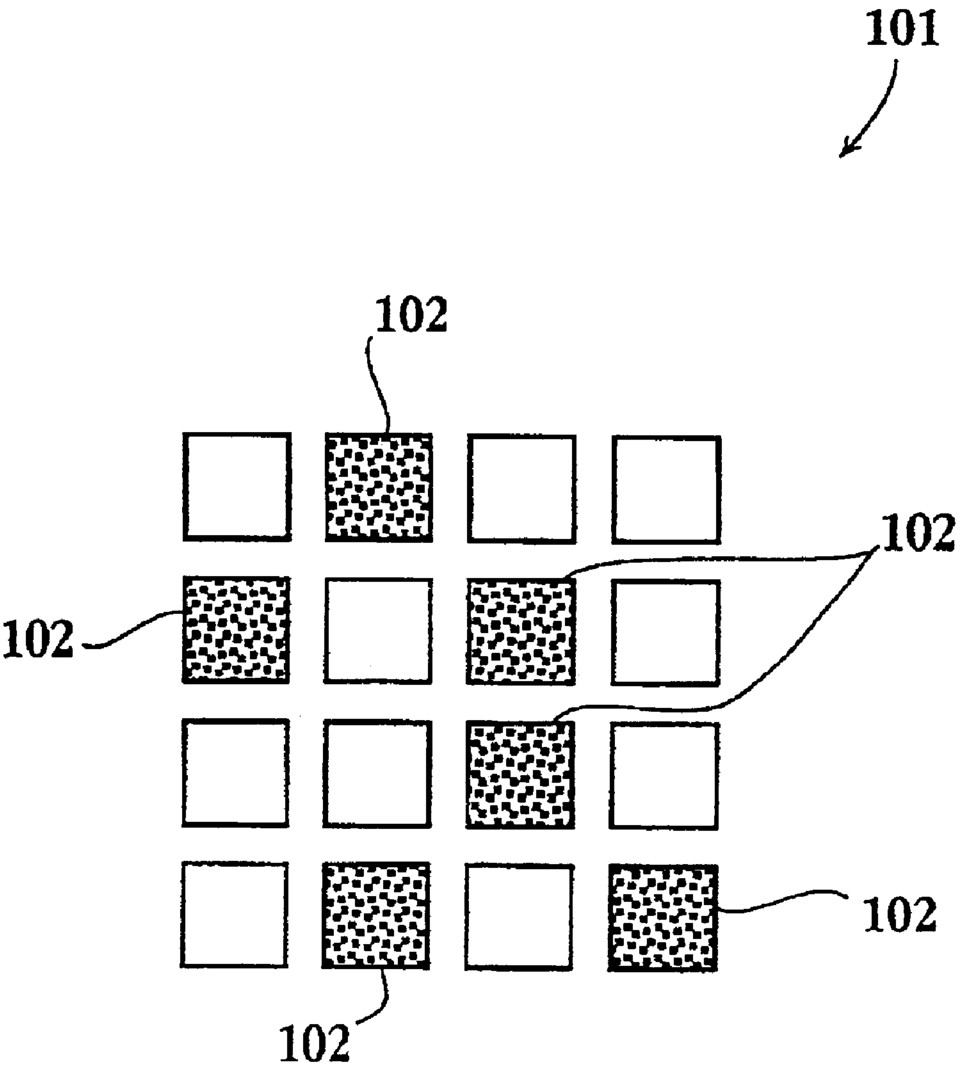
FIG. 1 depicts exemplary coded chip (101) having 16 bits of information encoding 65536 classes.

The invention provides for a chemical-library composition comprising a plurality of coded carriers, each having at least N>1 specified code positions and one of M>1 detectable indicia at each code position, such that each carrier can be identified by one of up to $M^N$ different code combinations, and a different known chemical compound carried on each different-coded carrier. The different compounds in the composition may be, for example, oligonucleotides having a known, defined sequence, oligopeptides having a known, defined sequence, small chemical compounds having known defined structural formulae, or targets such as receptors.

Other preferred embodiments have N>2, 3, 4, 5, 6, 7, 8, 9, and 10, and M>2, 3, 4, 5, 6, 7, 8, 9, and 10.

In another aspect, the invention includes a method of forming a library of determinable chemical compounds. The method comprises first placing into each of a plurality of separate reaction vessels, carriers having a selected one of a plurality of detectable code combination, each defined by one of N>1 specified code positions and one of M>1 detectable indicia at each code position, such that the carriers in any vessel all have one of up to $M^N$ different code combinations. The carriers are then reacted with reagents effective to form on the carriers, as solid-supports, a selected one of up to $M^N$ different known library compounds. The composition is formed by forming a mixture of carriers from different reaction vessels.

In still another aspect, the invention includes a method of detecting one or more target molecules capable of binding specifically to one or more different, known library compounds. The method includes the steps of (i) contacting the target molecule(s) with a chemical-library composition of the type described above, (ii) distributing the carriers for individual-carrier decoding, (iii) detecting carriers having bound target molecule(s) and (iv) decoding the carriers having bound target molecules, to identify the library compound(s) to which the target molecule(s) are bound.

In one general embodiment, each of the carriers is formed of N separate layers, each layer having one of M different color indicia. For example, each carrier may be a cylinder of stacked layers, where the cylinder diameters are in the 1 to 200 micron range. In another general embodiment, each carrier has a surface that is partitioned into N surface regions, and each region contains one of at least two different surface indicia. In still another embodiment, each of the carriers has a magnetic or para-magnetic layer or component that allows for magnetic separation and orientation of the carriers.

The invention further provides for a kit containing separated carriers for user compound addition containing individual populations of discrete carriers capable of being loaded with user-defined compounds. Compound containing carriers may then be mixed with other compound containing carriers to form user-defined libraries of compounds on carriers. Such compound libraries may then be screened according to methods described in this specification.

The invention further provides for an organized chemical-library array. The array comprises a plurality of coded carriers, fixedly organized in an array-forming device. Each coded carrier having at least N>1 specified code positions, and one of M>1 detectable indicia at each code position, such that each carrier is identifiable by one of up to $M^N$ different code combinations. And, a different known chemical compound carried on each different-coded carrier, and where the position of each coded-carrier is coordinated with a determined carrier identity and corresponding compound identity.

The invention further provides for a method of detecting one or more target molecules capable of binding specifically to one or more different, known library compounds. The method comprises contacting the target molecule(s) with a chemical-library composition composed of a plurality of coded carriers, each having N>1 specified code positions and one of M>1 detectable indicia at each code position, such that each carrier can be identified by one of up to $M^N$ different code combinations, and a different known library compound carried on each different-combination carrier, under conditions in which the target molecules can bind specifically to known library compounds. Then distributing the carriers for individual-carrier decoding. And, detecting carriers having bound target molecule(s) and decoding the carriers having bound target molecules, to identify the library compound(s) to which the target molecule(s) are bound.

The invention further provides for a coded particle for use in carrying out selected chemical or biological reactions or analyses, comprising (a) a plurality of self-orienting coded carriers, each having N>1 spatial code compartments and one of M>2 optically detectable indicia at each code compartment, so that each carrier can be optically identified by one of up to $M^N$ different code combinations, each of said M>2 indicia being a different color, and (b) a different known chemical compound carried on each different-combination carrier, wherein each of said carriers is formed of N separate layers or bundled fibers, each layer or bundled fiber having one of M different color indicia, said layers or bundled fibers form said spatial code compartments, and said carrier are formed in a shape adapted to self orient into a carrier holder within an holder array to expose said spatial code to a optical window within said holder, said window in optical communication with a detector for reading said spatial code.

In another aspect, the invention provides for the coded particle above wherein the carrier has a cross sectional shape selected from the group consisting of; circles, triangles, squares, hexagons, octagons, decagons, polygons, and/or where at least one carrier is embedded in a larger spherical structure, wherein said code is readable from and external surface of said spherical structure, said structure is adapted to hold compounds, cells, or biological materials. The coded particles above may also have the carrier be self orientating by virtue of a portion of said carrier being susceptible to attraction or repulsion by a force selected from the group consisting of gravity, electrostatic forces, electrophoretic forces, dielectric forces, and magnetism.

The invention further provides, an apparatus for detecting activity on the coded carrier above, and determining said code, comprising, a carrier holder array, said carrier having a plurality of holders distributed therein, said holders adapted to hold said carriers so that said coded carriers code faces an optical window in optical communication with a detector, said window situated within said holder to optically detect at least one surface of said carrier, said at least one surface displaying said spatial code, wherein when said carrier is held in said holder after said carrier is positioned within said holder, said detector is able to detect at least one activity on said carrier, and said detector is able to detect said spatial code of said carrier. The apparatus above, wherein said carrier is self-orienting, and said holder is adapted to self-orient said carrier so that at least one spatial code is detectable by said detector.

The invention further provides for a method of multiplexing the detection and quantification of analytes. The methods comprises the steps of distributing on a surface a plurality of coded carriers having different compounds attached to different carriers. Then scanning the surface for carriers having a detectable reporter, recording the positions of the carriers having a detectable reporter, determining the code for each carrier at each recorded position.

The invention also provides an array device. The device comprises a surface, and a plurality of coded carriers having different compounds attached to different carriers, wherein the carriers are randomly distributed upon the surface.

These objects and features of the invention will become more fully apparent when the following detailed description of the invention is read in conjunction with the accompanying drawings.

DETAILED DESCRIPTION OF THE INVENTION

The invention provides for a chemical-library composition comprising a plurality of coded carriers, each having at least N>1 specified code positions and one of M>1 detectable indicia at each code position, such that each carrier can be identified by one of up to $M^N$ different code combinations, and a different known chemical compound carried on each different-coded carrier. The different compounds in the composition may be, for example, oligonucleotides or peptide nucleic acids having a known identifiable characteristic (usually the nucleotide sequence), oligopeptides having a known identifiable characteristic (usually the amino acid sequence), small chemical compounds having a known identifiable characteristic (usually the structural formula), or targets such as receptors.

The term position is defined broadly as including spatial relationships such as linear relation, two-dimensional relation, and three-dimensional relation. Preferred embodiments define position as two-dimensional, or three-dimensional, but not linear relation. Other embodiments of the invention provide for position as being a temporal relation such as in timing between events. A position, therefore, exists relative to another position. In yet other embodiments, each position included greater than four or five indicia. And in still other embodiments, each position does not contain nucleic acid indicia. And in yet still other embodiments, indicia are only optically detectable. In other embodiments, position is not meant to include ranking.

In another aspect, the invention includes a method of forming a library of determinable chemical compounds. The method comprises first placing into each of a plurality of a separate reaction vessels, carriers having a selected one of a plurality of detectable code combination, each defined by one of N>1 specified code positions and one of M>1 detectable indicia at each code position, such that the carriers in any vessel all have one of up to $M^N$ different code combinations. The carriers are then reacted with reagents effective to form on the carriers, as solid-supports, a selected one of up to $M^N$ different known library compounds. The composition is formed by a mixture of carriers from different reaction vessels.

The carriers placed in each reaction vessel may each be formed, for example, of N separate layers, each layer having one of M different color indicia. The reacting may include the steps in a stepwise oligomer synthesis reaction that are effective to form oligomers with known defined sequences on the solid-support carriers.

The invention provides a method of forming a library of determinable chemical compounds. The method comprises the steps of placing into each of a plurality of separate reaction vessels, carriers having a selected one of a plurality of detectable code combinations. Code combinations are defined by one of N>1 specified code positions, and one of M>1 detectable indicia at each code position, such that all carriers in any vessel will all have one of up to $M^N$ different code combinations. Then reacting the carriers in each vessel with reagents effective to form on the carriers acting as solid-supports, a selected one of up to $M^N$ different known library compounds, and forming a mixture of carriers from different reaction vessels.

The invention further provides for an organized chemical-library array. The array comprises a plurality of coded carriers, fixedly organized in an array-forming device. Each coded carrier having at least N>1 specified code positions, and one of M>1 detectable indicia at each code position, such that each carrier is identifiable by one of up to $M^N$ different code combinations. And, a different known chemical compound carried on each different-coded carrier, and where the position of each coded-carrier is coordinated with a determined carrier identity and corresponding compound identity.

The invention yet further provides a method of detecting one or more target molecules capable of binding specifically to one or more different, known library compounds. The method comprises contacting the target molecule(s) with a chemical-library composition composed of a plurality of coded carriers. Each coded carrier having N>1 specified code positions and one of M>1 detectable indicia at each code position, such that each carrier is identifiable by one of up to $M^N$ different code combinations. And, a different known library compound carried on each different-combination carrier, under conditions in which the target molecules can bind specifically to known library compounds. Then distributing the carriers for individual-carrier decoding, and detecting carriers having bound target molecule(s) and decoding the carriers having bound target molecules, to identify the library compound(s) to which the target molecule(s) are bound.

In still another aspect, the invention includes a method of detecting one or more target molecules capable of binding specifically to one or more different, known library compounds. The method includes the steps of (i) contacting the target molecule(s) with a chemical-library composition of the type described above, (ii) distributing the carriers for individual-carrier decoding, (iii) detecting carriers having bound target molecule(s) and (iv) decoding the carriers having bound target molecules, to identify the library compound(s) to which the target molecule(s) are bound.

More generally, in use, the method of the invention is designed for detecting one or more target molecules capable of binding specifically to one or more different, known library compounds. In practicing the detection method, the target is contacted with the library composition of the invention, that is a chemical-library composition composed of (i) a plurality of coded carriers, each having N>1 specified code positions and one of M>1 detectable indicia at each code position, such that each carrier can be identified by one of up to $M^N$ different code combinations, and (ii) a different known library compound carried on each different-combination carrier. Contacting is carried out under conditions in which the target molecules can bind specifically to known library compounds. For example, in the case of polynucleotide target binding or oligonucleotide-coated carriers, the contacting is carried out under conditions in which the target can bind by hybridization to complementary-strand oligos on the carriers.

Another aspect of the invention provides a composition for multiplexed analysis of one or more different known cell populations comprising:

a plurality of coded carriers, each formed of N>1 ordered spatially distinct compartments, and each compartment having one of M>1 detectable indicia, such that each carrier can be identified by one of up to $M^N$ different code combinations, and a different known cell population attached to each different carrier.

Another aspect of the invention provides a composition for multiplexed analysis of one or more different known cell populations comprising:

a plurality of coded carriers, each formed of N>1 ordered spatially distinct compartments, and each compartment having one of M>2 detectable indicia, such that each carrier can be identified by one of up to $M^N$ different code combinations, and a different known cell population attached to each different carrier.

Another aspect of the invention provides a microparticle for carrying and identifying one or more compounds or biological entities attached thereto, comprising:

a coded carrier, said coded carrier having a spatial optical code formed therein, said code having N>1 spatially distinct compartments, and each compartment having one of M>2 spectrally distinct detectable indicia, such that each carrier can be identified by one of up to $M^N$ different code combinations, and one or more known compounds or biological entities attached to said carrier, said compounds or biological entities having at least one identifying feature, wherein said code correlates to said identifying feature of said compounds or biological entities, to identify such compounds or biological entities.

Another aspect of the invention provides an apparatus for analyzing events occurring on or adjacent a microparticle containing an identifying code having at least one code viewing surface, comprising:

one or more fiber optic receivers, said receivers having an outer cladding and an inner core, said outer cladding protruding at one end from said inner core to form at least one wall of a receiver area for receiving and orienting said microparticle so that at least one code viewing surface of said identifying code faces said end of said fiber optic receiver, a detector, said detector for detecting said events occurring on or adjacent said coded microparticle, said detector being in optical communication with said inner core, a reader, said reader for reading said code from at least one code viewing surface, said reader being in optical communication with said inner core, wherein said receiver area holds said particle so that said code's viewing surface is readable by said reader, and said events are detectable by said detector, while said microparticle resides within said receiver area.

The carriers, some of which have bound target, are then distributed for individual-carrier decoding. In the example described above, cylindrical carriers are distributed for carrier flow through a capillary flow path. Alternatively, the carriers may be examined or scanned, e.g., by light microscopy or raster scanning, according to methods employed for DNA-chip scanning.

The scanning is operable to detect carriers having bound target. The target may be detectable in native form, or may be labeled, e.g., by fluorescent label, for detection. Carriers having bound target are then scanned to decode the carriers, allowing the specific compound carried on the carrier to be identified.

It will be appreciated that this method can be used in any application currently employing position-addressable arrays of compounds, for example, oligonucleotides, but in a much simpler, less expensive format.

Carriers and analytes may interact in a tube and may be deposited on the slide for "reading" purposes. The manufacturing process consists of producing different classes of carriers and coating them with different probes. For example, microbeads could be used as carriers since the manufacturing of microbeads of different size and color is well developed and the beads are commercially available from several sources (Bangs Laboratories, Fishers, Ind.; Molecular Probes, Eugene, Oreg.). Coating of beads with DNA and other reagents is also a common procedure (Bangs Laboratories, Fishers, Ind.; Luminex Corp., Austin, Tex.). Furthermore, beads have been used in flow cytometry also to analyze reaction products.

Another embodiment of the carriers is based on Multilayer Soft Lithography (Marc A. Unger, Hou-Pu Chou, Todd Thorsen, Axel Scherer, Stephen R. Quake "Monolithic Microfabricated Valves and Pumps by Multilayer Soft Lithography" Science v. 288, pp.113–116, 7 Apr. 2000). This method can be amended to use differently dyed resins as layers. After a sheet of multilayered silicone is made, it can be "cut" in parallel into squares or cylinders by exposing it to eximer laser light (service provided by Resonetics, Inc. www.resonetics.com). Other references that teach microfabrication and fiber optics include and are entirely incorporated by reference herein, Fundementals of Microfabrication, by Marc Madou, CRC Press (1997); Fiber Optic Networks, by Paul Green, Prentice-Hall (1993); Nonlinear Fiber Optics, by Govind Agrawal, Academic Press (1995; Microparticles can be made by an adaptation of the soft lithography as described by Unger, et al. in Science volume 288, page 113–116, April 2000, where multiple layered substrates are etched to form microparticles having on at least one side a viewable coding region.

Unsuggested advantages of smaller carrier size since carriers are pre-encoded by virtue of the method for which they are manufactured. Such manufacturing permits bulk preparation.

Miniaturization provides for smaller sample sizes, better kinetics in solution. Miniaturization achieved by the present invention exceeds that obtained by optical burn in technology, e.g., CD-ROM, or printing technology as in micro-injet printing.

The code on a carrier is more permanent because the code exists throughout the structure and therefore is not susceptible to change as a result of chemical synthesis, processing, handling or mechanical stress, in many cases, thermal stress and degradation by exposure to electromagnetic radiation such as ultraviolet light.

Coding material may be made in a wide array of colors, optical characteristics, and combinations of colors and optical characteristics. Consequently, greater information content is achieved with fewer coding positions as compared to traditional binary bar code formats. In preferred embodiments, each code indicia has a different optical or spectral signature, detection resolution is increased since a detector relies on spectral character more than intensity as in standard uniform product code bar code reader systems or optical encoding as in compact disk storage systems.

Spatial coding, using spectrally distinct indicia, provides for increased information content than systems using colorimetric blends where the entire code is a single spectral code. For example, the present invention provides, in some embodiments, spatially coded carriers, where each code comprises N coding positions having one of M indicia at each code position, wherein each code is an optically distinct code having different spectral character than the other indicia. Thus, unlike a simple black and white code where there is simply a difference in intensity between each indicia, but no difference in spectra, the present invention provides for each different indicia to have a different spectral quality such as color. Higher information content is realized for a given coding surface area, hence, smaller spectrally coded carriers may be used to encode larger libraries compared to the library size that a larger binary coded carrier could encode.

In one preferred embodiment, a cuboidal carrier is made from a first set of layers sandwiched together to form a cross-sectional code, and then flanked on opposing sides with yet another sandwich code so that every face of a sectioned of portion of the carrier displays the sandwich sequence or code.

In yet other embodiments, milifiori or milli fiori glass manipulating techniques are employed to impart a distinguishing shape upon the cross section of each coding region. For example, a star cross-section fiber is fused with a cladding to form a carrier having a colorimetric identifier or other optical identifier, and a spatial code of a star shape. Such coding impart a third level of coding to the carrier, that is, shape within a shape. Other shapes may be used, preferably in combination with other shaped fibers.

In yet another embodiment, nano-crystals are used as indicia to provide narrow bandwidth emission for low optical spill-over detection between coding regions of a spatially code. In particularly preferred embodiments, the nano-crystals are embedded in the matrix of a fiber or filament to form an optically responsive fiber or filament for use in forming the fiber bundles that are sectioned into coded carriers.

Preferred embodiments of the present invention offers advantages over standard lithographic technologies because miniaturization is achieved by stretching the length of fibers to reduce the cross-sectional diameter of fiber bundles containing the fibers.

Another extension of the above method is molding of two complementary patterned surfaces of differently colored resins. When such surfaces are fused together and cut, this results in flat carriers with a pattern of predominantly the first or the second color, see FIG. 14.

Figure 14:
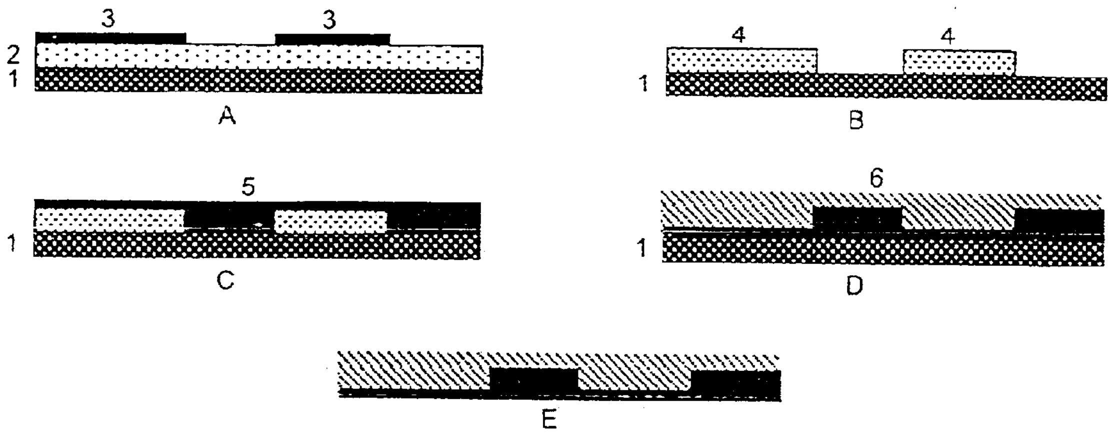
FIG. 14 depicts carriers formed by soft lithography.

FIG. 14 depicts the process and product of soft lithography, as described by Unger, et al., Science 288:113, Apr. 7, 2000, incorporated in its entirety by reference herein. In FIG. 14, A: Photoresist (2) is applied to a rigid substrate (1) and covered by a photomask (3). B: Photoresist is solidified after exposure to light and serves as a mold (4). C: An elastomer (e.g., GE Silicones RTV 615) with added contrasting agent is spin-coated on the mold and baked (5). D: The resulting layer (5) is peeled of the substrate (1), turned upside down, and placed on the substrate (1), then spin-coated with the same elastomer without addition of the contrasting agent, and baked (6). E: The two-layer sheet is peeled and cut into encoded carriers.

Carriers may also be composed of plastics and shaped by processes such as injection molding or extrusion, or from other substrates by micro-engineering processes (e.g.—MEMS—micro-electric mechanical systems) familiar to those skilled in the art. Micro-injection molding of small detailed parts such as micro-gears is commercially available. Using this method, the identifying indicia incorporated into carrier particles may include the formation of various shapes or lines, and/or by the location of processes located about the periphery of the carrier, such as the specific relative placement of "gear teeth" about a gear. Similarly, the use of plastics such as polymethylacrylates in plastic optical fibers makes possible methods of producing carriers analogous to that used to prepare carriers from glass fibers.

Figure 15:
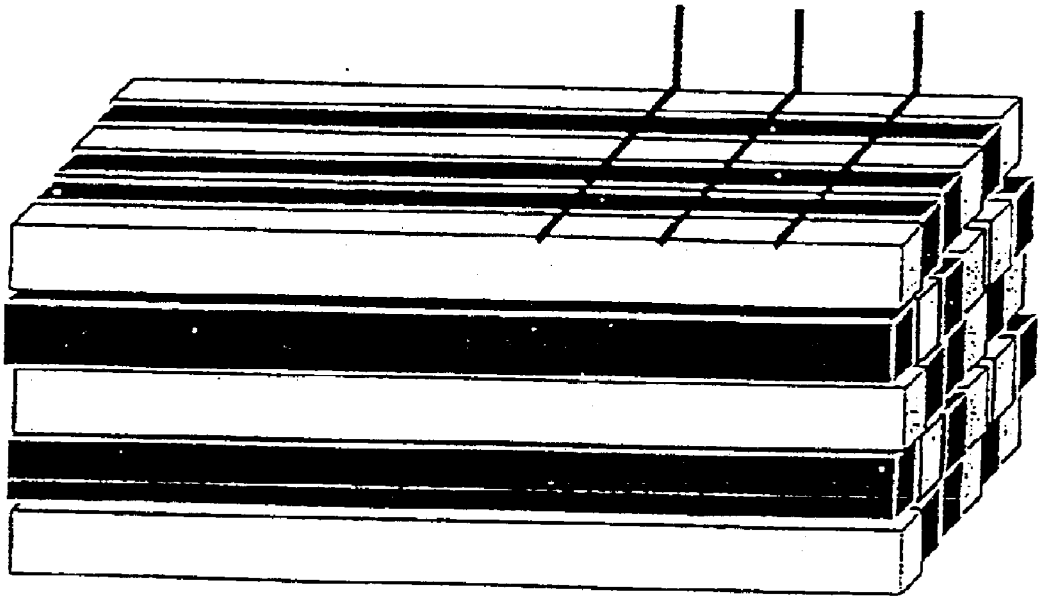
FIG. 15 depicts carriers made from fibers.
Figure 16:
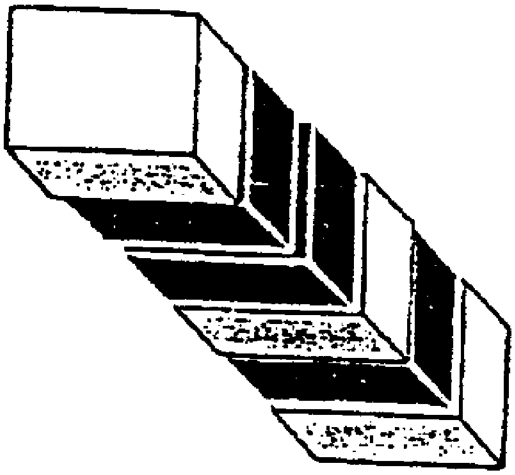
FIG. 16 depicts carriers made from fibers.

A preferred use of particle area can be achieved with a 2-dimensional fiber, cut in 10–20 ($\mu$m slices as in FIGS. 15 and 16. The assembly could be made rectangular to have only two possible starting reading points, like in one-dimensional ribbons or multilayer particles (assume that reading always starts from a comer along the longer side). One approach to uniquely identifying a class is to use not all possible codes, but treat the codes that are reversals of each other as the same. This results in a little over a half of all codes usable. FIG. 16 depicts a preferred carrier for use in flow-based applications, where the fibers are cut to produce bands along the length.

Figure 17:
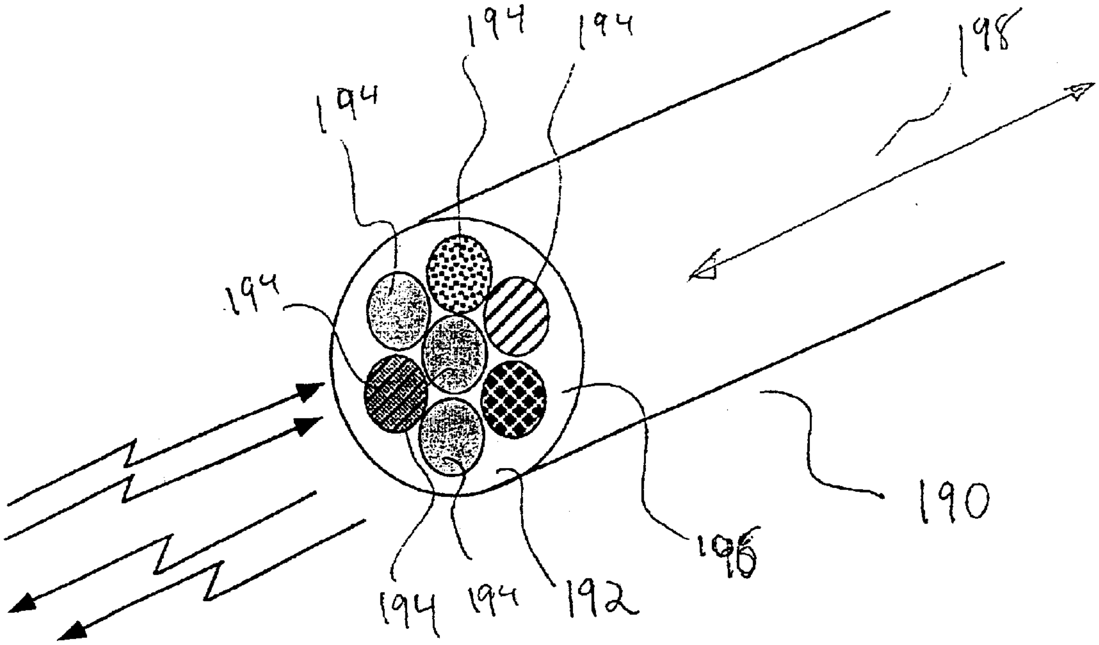
FIG. 17 depicts a coded carrier.

A particularly preferred embodiment provides for end viewable codes within the carrier so that a code may be determined by viewing either the top or bottom surface of, for example, a cylinder shaped carrier. In this particularly preferred embodiment, the code comprises concentric rings co-axially positioned around the central, cylindrical axis of the cylinder carrier. FIG. 17 depicts a perspective view carrier 190 comprised of fused bundle 192 of fibers 194, where at least two of the fibers comprise optical, spatial coding compartments, where each of the fibers are aligned in a parallel fashion, parallel to axis 198 of the cylinder formed by the fused bundle. In the shown embodiment, as disclosed by Chee, is used to retain spherical particles that are encoded as a whole either colorimetrically or chemically, including DNA.

The approach described above is similar to that disclosed by Chee, WO 99/67641, filed as U.S. patent application Ser. No. 09/189,543 which is entirely incorporated by reference herein. In Chee, optical fibers having an outer cladding surrounding an inner core, where the inner core has been selectively etched back to produce cavity which forms a carrier holder. This arrangement, as disclosed by Chee, is used to retain spherical particles that are encoded as a whole either calorimetrically or chemically, including DNA.

The present invention provides, in one embodiment, an improvement to Chee comprising substituting the spherical carriers of Chee with the axially coded cylindrical carriers of the present invention, described above. Furthermore, we propose substituting the simple detector of Chee which only detects intensity and color of the spherical carrier as a whole with a detector adapted to detect the spatial position of each code compartment of the carrier to determine the carrier code identity, and thus the identity of the compound or other material carried on the surface of the carrier. This improvement overcomes the limitations of Chee where each carrier must decoded chemically, including by decoding the DNA tag, or being limited to a relatively small number of different carrier species because the coding system is greatly limited in comparison to the present invention. By using spatial or positional codes as described herein, exceedingly large arrays of different carriers may be analyzed in a parallel format, where the identity of the carrier is determined by reading an optical, spatial code from the arrangement of the coding compartments.

Figure 18:
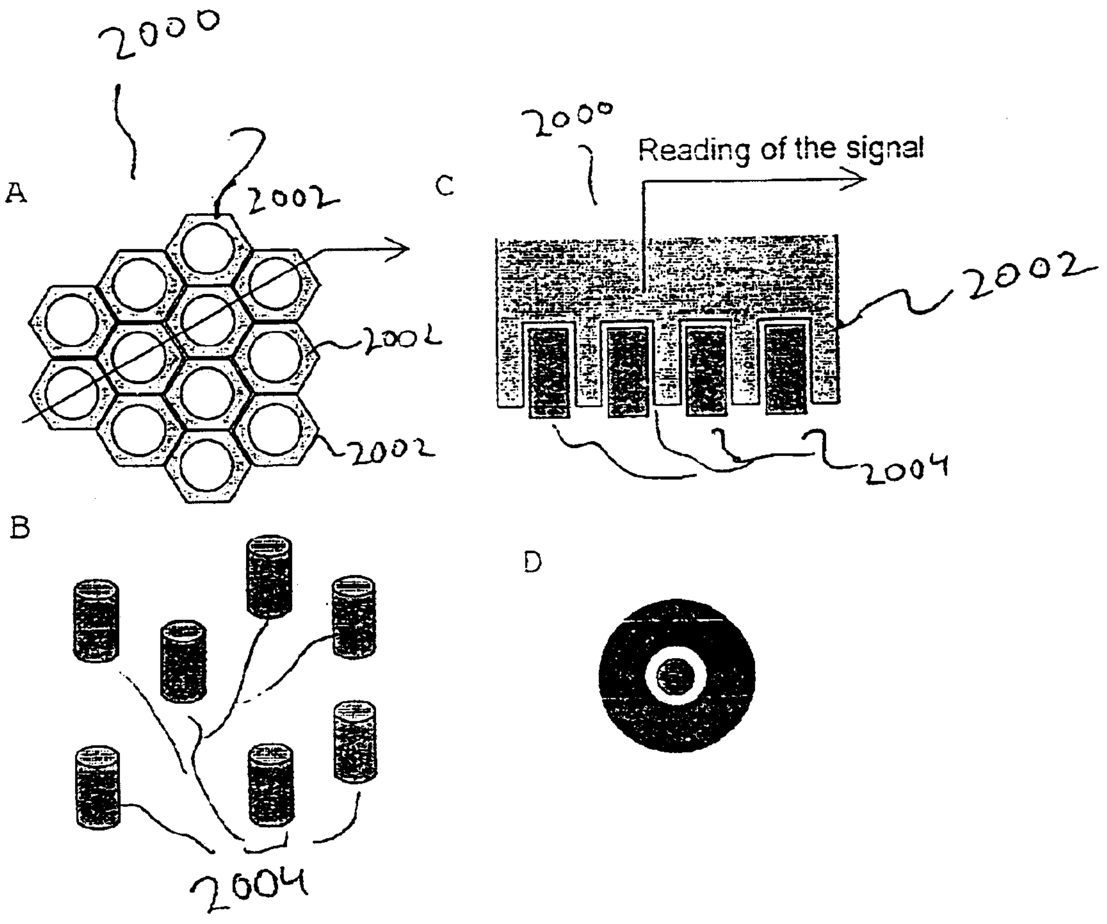
FIG. 18 depicts a a holder array adapted to support one or more self-orienting carriers.

The present invention further provides for a detection system where in one embodiment, comprises the optical fibers of Chee in optical communication with a detector of the present invention adapted to detect both activity on the surface of a carrier, and detect the code within the carrier. In another embodiment, holder array 2000, as shown in FIG. 18, having a plurality of holders 2002 adapted to hold a self-orienting shaped carrier 2004 is detachable from the fiber optics in optical communication with the detector so that the multiple holders may be used with one fiber optic-detector device. In yet another embodiment, carriers 2004 having compounds or materials attached thereto are manufactured and distributed pre-installed in a holder device that may later be combined with the fiber optic-detector described above. In yet another embodiment, the pre-installed carrier holders are pre-characterized with respect to positional relation between compound and position of each carrier within the holder array so that an end user is relieved of having to decode each carrier, and only needs to measure activity associated with each carrier and use a database associated with each holder array, provided by the manufacture, to determine each carrier's code and identity.

For the analysis of the binding of target, the carriers may be distributed in the random fashion or may be distributed by placing them at discrete locations on a substrate surface, where the detecting and decoding steps may be carried out by a detector operable to scan the substrate surface.

If the carriers are multilayered color carriers, one possible approach to their identification is as follows. A histogram of directions of layers present in the image above the brightness threshold of carriers is constructed. The areas of similar orientation are found by double-sided thresholding from the peaks of the direction histogram. These areas are then analyzed by means of Mathematical Morphology described in Serra, "Image Analysis and Mathematical Morphology", Vol. 1. Academic Press, London, 1989, herein incorporated in its entirety by reference, to remove noise and test their shape to determine if the resulting areas are candidates for reading the code. Once the carriers are segmented and their orientation known, a projection of the image on the line perpendicular to the bands can be calculated. Profiles of this projection in each color are analyzed, the bands identified, and the code extracted according to the relative brightness of the bands in each color. All carriers have the same number of bands, and possibly not all code combinations are used for redundancy and error correction. The carriers with fewer than normal number of bands are rejected. The code is then tested on the error condition and rejected or corrected. Error correcting codes were developed in information theory described in Pless, "Introduction to the Theory of Error-Correcting Codes", Wiley, New York, 1982, herein incorporated in its entirety by reference.

The preceding paragraphs deal with image processing required to identify a carrier as belonging to a certain carrier class. The second task is to measure one or more reporting modalities, e.g., one or more fluorescent colors, or one or more absorptive colors for each carrier. This can be done essentially with the same image processing methods, e.g., correcting the background and calculating the integrated intensity within the carrier mask. The more accurate approaches may be 1) taking pixelwise ratios of fluorescent colors and then averaging it within the carrier, or 2) taking the linear regression coefficient as described in Korn, et al., "Mathematical Handbook for Scientists and Engineers", McGraw-Hill, New York, 1961 of one reporting color to another reporting color on the pixels belonging to the carrier or to a part of the carrier designated for measurement. In competitive hybridization scheme the above mentioned linear regression coefficient is the sought after parameter. It is desired to evaluate this parameter with as little error as possible. Since segmentation of the carriers by thresholding or any other means may not be accurate, it is suggested to use the error of linear regression coefficient as the basis of final segmentation. This error is determined statistically on all pixels, which belong to the carrier (or part thereof as mentioned above). The refined segmentation is achieved in a sequence of approximations that systematically modifies the outline of the carrier to minimize the error of linear regression coefficient. This process may be constrained by conditions like minimal and maximal number of pixels, or connectivity, or shape of the outline. The additional benefit of this approach is that the resulting error can be used as a measure of confidence of the regression coefficient.

Another useful application of the invention is in conjunction with probes known as molecular beacons described in U.S. Pat. Nos. 6,037,130 and 5,118,801, Tyagi, et al. F.R. (1996), Nature Biotechnology 14: 303–308, and Fang, et al. (2000) "Advances in Nucleic Acids and Protein Analysis". Proceedings of SPIE 3926:2–7 each herein incorporated in their entirety by reference. Molecular beacons are two-state probes containing both a fluorochrome and a quenching moiety. When not hybridized to a target molecule, molecular beacons form a hairpin structure bringing the fluorochrome into close proximity to the quencher and thereby quenching fluorochrome signal. Hybridization to a target molecule causes the hairpin structure to open, spatially separating the fluorochrome and quencher and resulting in a hybridization-dependent signal. These probes can be attached to the carriers by a biotin-avidin linkage or other chemical linkage of appropriate length that keeps the beacon molecule from physically interacting with the surface of carrier.

The methods/compositions described herein are also immediately compatible for use with dendrimer-type probe systems (Stears, Robin L., Getts, Robert C., and Steven R. Gullans. A novel, sensitive detection system for high-density microarrays using dendrimer technology. Physiol Genomics 3:93–99, 2000). This technology is particularly suited to Comparative Genomic Hybridization (CGH) applications involving very low levels of gene expression.

An example of a particularly advantageous combination of carrier and molecular beacon technologies relates to clinical diagnostics and pharmacogenetics. Carriers can be prepared where each class of carriers has attached to it multiple types of molecular beacon probes, where each probe type contains a different fluorochrome signal. In use, each carrier class could, for example, contain the molecular beacon probes for all the clinically relevant alleles for a particular liver enzyme, with each allele probe containing a different fluorochrome. Upon receipt of a patient sample and specific instructions, a panel of appropriate tests for the alleles of specific liver enzymes can then be quickly assembled and performed. The patient's alleles for each liver enzyme is then determined by analyzing the fluorescence emission wavelengths associated with each class (code) of carrier.

The invention further provides compositions where the carrier coding element is a piece of a flat ribbon made of parallel glass fibers, and each fiber has one of at least two different colors, refractive indices or other optical properties. The invention further provides a method of fabricating carrier codes made from fiber optic components, such as faceplates, windows, image conduits are well developed as described in Hecht, "Understanding Fiber Optics", 3 edition, 1998, Prentice Hall, herein incorporated in its entirety by reference. Individual fibers can be in the range from 3 μm to 100 μm. Optical fibers can be fused together to form structures consisting of a multitude of fibers in a variety of geometries. In manufacturing, starting with pre-forms fiber assemblies are drawn under heat and pressure such that they are parallel to each other; they retain shape and relative dimensions when drawn to a smaller size. Fibers can be made of transparent or colored glass or plastic. This embodiment of the encoded carriers does not focus on using fibers for optical purposes, which makes their manufacturing easier and widens the choice of materials. In the present embodiment square fibers of transparent or colored glass or plastic are assembled in a flat ribbon preform. The order of differently colored fibers defines the code. The number of fibers depends on the desired number of classes to be encoded and the number of available colors. For example with just two colors 16 fibers could encode 64K classes. The assembly is then drawn to the size of approximately 100 μm across the ribbon and cut into segments of approximately 200 μm to 300 μm. Cutting could be done individually by a laser, or after ribbons of the same class have been assembled in a bunch by a saw.

A particularly preferred embodiment of the invention provides for encoded carriers incorporating nanocrystals prepared for use as fluorescent probes. Semiconductor nanocrystals, compared with conventional biological fluorophores like fluorescien and phycobili proteins, have a narrow, tunable, symmetric emission spectrum, are excitable at any wavelength shorter than the emission peak, and are photochemically stable. Fluorescence emission for these nanocrystal fluorophores is dependent on variations in the material composition and physical size as described in Brus, J.Phys.Chem, 98:3575 (1994) and Bruchez et al., Science, 281:2013–2016 (1998), both herein in their entirety by reference. In other words, a series of nanocrystal probes can be created that cover a wide emission spectrum from 200 nm to 2 μm, with narrow emission widths around 20 nm, that in turn can be mixed or doped into specific encoding regions of the described carriers. The whole group of different emitting nanocrystals located in defined encoded regions are excitable at a single wavelength. Just as in the case of differential spatial coding by color or other fluorochromes, the nanocrystals extend the range of possible detected classes by taking advantage of the narrower emission and single excitation criteria.

A preferred embodiment would incorporate the 3 nm CdSe nanocrystals described in Nirmal et al. Nature, 383: 802 (1996), herein incorporated in its entirety by reference, in one encoding position and 4.3 nm InP nanocrystal in another position. Using UV light excitation, or any wavelength below the emission peak of the highest energy emitting crystal in use, the fluorescence of the two different classes of crystal can be detected and their spatial or positional encoding recorded. In another manifestation using time-gated detection, the fluorescence lifetime can be recorded, which may help with eliminating autofluorescence and background.

The invention further provides for encoded carrier "chips" containing an embedded code. The carriers can be of the same overall size and shape, but coding provides for practically unlimited number of carrier classes.

FIG. 1 depicts exemplary coded chip (101) having 16 bits of information encoding 65536 classes. Identification feature (102) encodes one bit. Identification features are different by an optical property, for example, transmission or reflection. The nominal size of each identification feature is between about 2 to 4 square $\mu$m.

The manufacture of such microchips, containing optically identifiable marks, is a standard practice in the microelectronic industry. See generally, "Semiconductor Materials and Process Technology Handbook", G. E. McGuire—ed., Noyes Publications, Park Ridge, N.J., USA, 1998, herein incorporated in its entirety by reference.

Figures 2A, 2B, 2C, 2D, 2E, 2F, 2G:
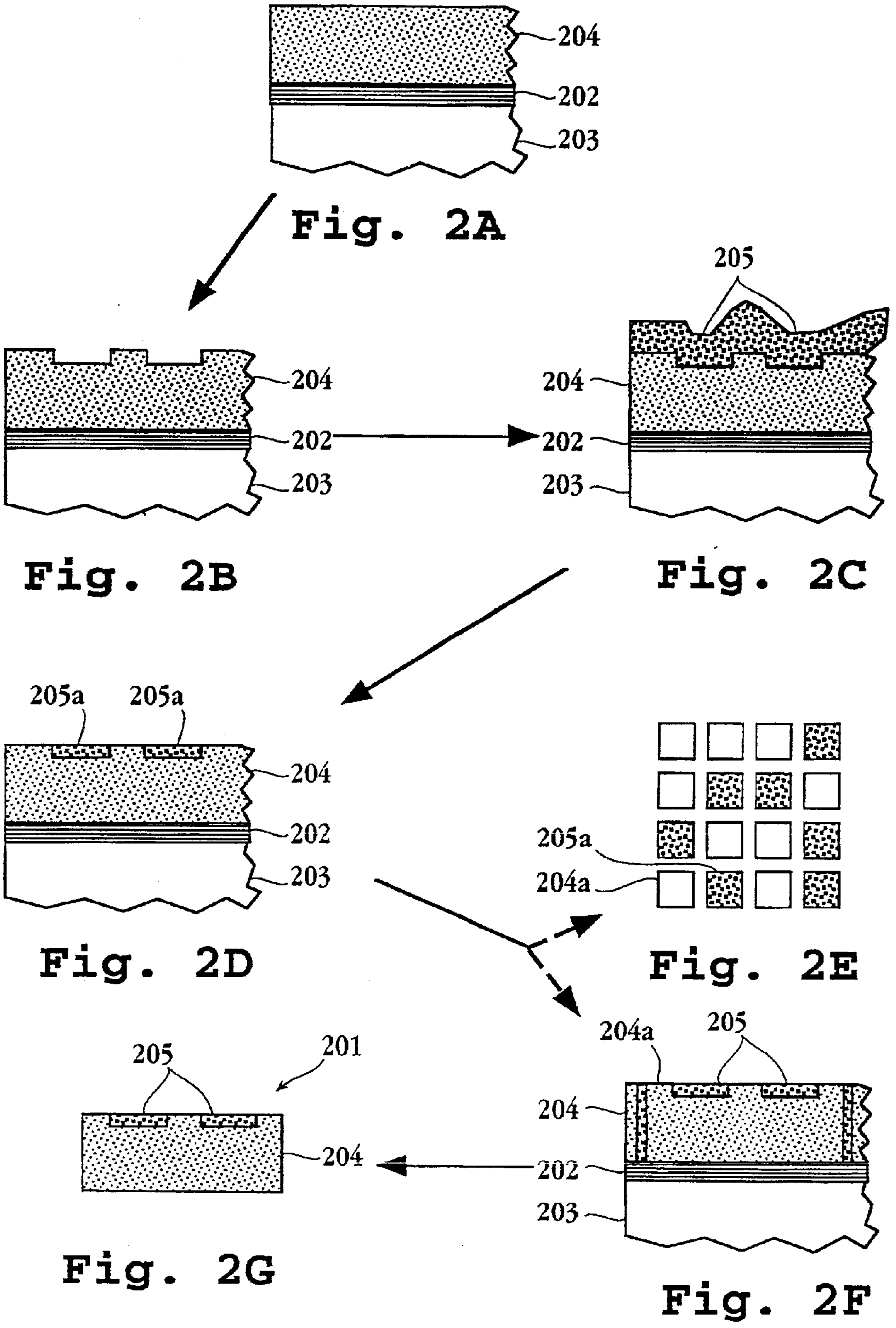
FIG. 2 provides an exemplary method for manufacturing coded chips.

FIG. 2 provides an exemplary method for manufacturing the coded chips of the instant invention where coded chip (201) may be produced, for example, by depositing, 0.5 $\mu$m Plasma Enhanced Tetra-Ethyl-Ortho-Silicate (PETEOS) (202) on silicon wafer (203) followed by the deposition of 2 $\mu$m polysilicon film (204). Polysilicon film (204) is patterned by a standard photolithography operation (not shown) using a special mask (not shown), which defines identification features **(205*a*). In FIG. 2*b*, plasma etching, removes approximately 0.5 ($\mu$m polysilicon film (204) in the areas previously patterned to provide the recess for the next deposition step. In FIG. 2*c*, identification feature film (205) is deposited onto the now patterned polysilicon film (204) and will provide contrast to polysilicon (204) and, therefore, the desired identification marks. Identification film (205) could be silicon nitride or a metal film (aluminum or tungsten) for the inspection in transmitted or reflected light. In the case of a metal film, metal in the film is removed by chemical mechanical polishing (CMP), leaving metal only in the recessed areas, see FIG. 2*d*. The next photolithography step, FIG. 2*e* and 2*f*, will define the boundaries of coded chip (201), and polysilicon (204) will be etched through to PETEOS (202). Then, wet etching in dilute (50:1) Hydrofluoric (HF) acid will release the microchips from the substrate, see FIGS. 2*f* and *g***.

Coded chip code determination is achieved by pattern matching—a method commonly used in machine vision. Each code forms a pattern of dark and light squares and could be matched against each carrier, with the closest match giving the carrier class number. There are commercially available packages that implement this type of processing, for example, Matrox Imaging Library, PatMax object location software, and Vision Blox—machine vision software. Alternatively, a specific algorithm can be developed to directly read the code from the carrier image. For example, such algorithm could comprise the following steps: correcting for background non-uniformity, setting a threshold at a level that distinguishes coded chips from the background noise, adjusting for image gaps, approximating rectangles and rejecting images if their actual shape deviates from a rectangle (in the event of overlapping carriers), rotating the image to normalized orientation, measuring to average image value in the middle of subsquares, and determining the code.

The invention further provides for the use of taggants as coded carriers. In this embodiment, the coded carriers to which the library compounds are attached are taggant particles, such as disclosed in U.S. Pat. Nos. 4,053,433, of which is herein incorporated in its entirety by reference. These particles are typically 1–200 micron size range and are formed of a plurality of N layers, each layer having one of M colors, allowing $M^N$ different coded carriers. Alternatively, the taggants may have different combinations of isotopes, radioisotopes, fluorescent labels, or compounds releasable in vapor phase, as described, for example, in U.S. Pat. Nos. 5,760,394, 5,409,839, 5,222,900, 4,652,395, and 4,363,965, each of which is herein incorporated in their entirety by reference. Color-coded taggants may be made, in accordance with the invention by forming multilayered sheets, as illustrated below, and processing the sheets into a desired shape.

Figure 3:
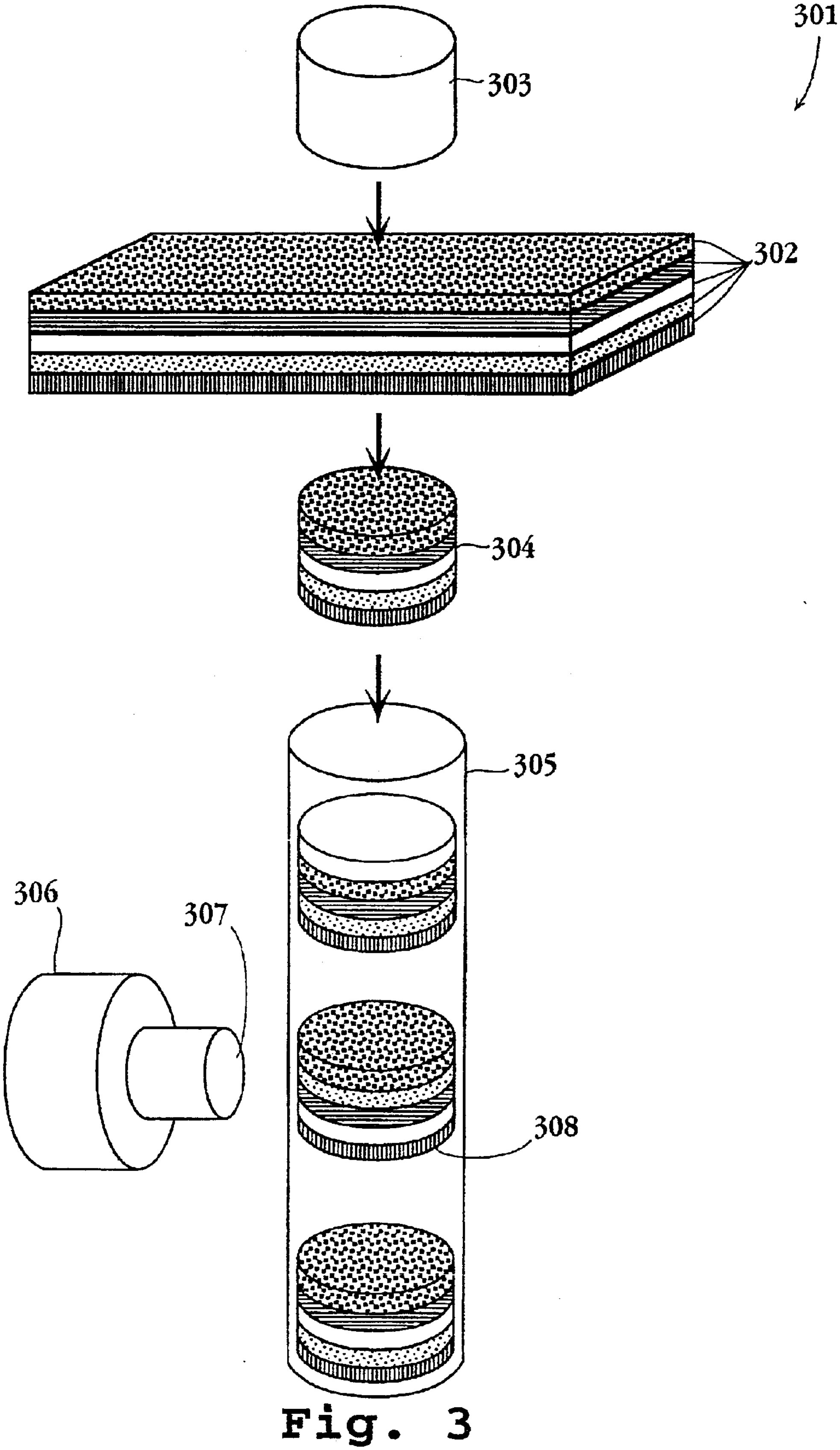
FIG. 3 depicts one preferred embodiment of using layered taggants as carriers.
Figure 4A:
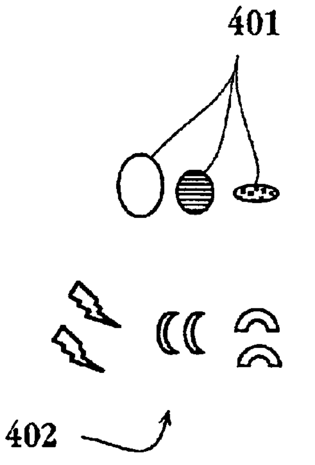
FIG. 4 depicts a method for comparative hybridization analysis.
Figure 4B:
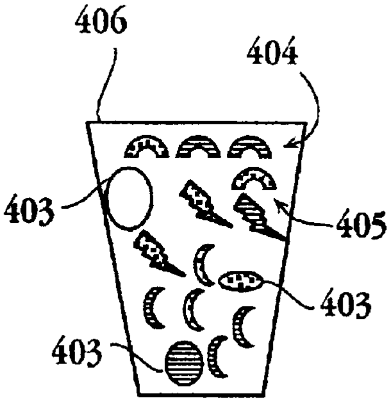
Figure 4C:
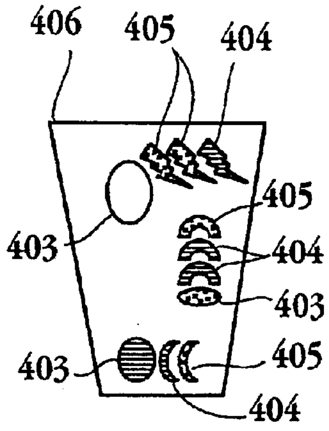
Figure 4D:
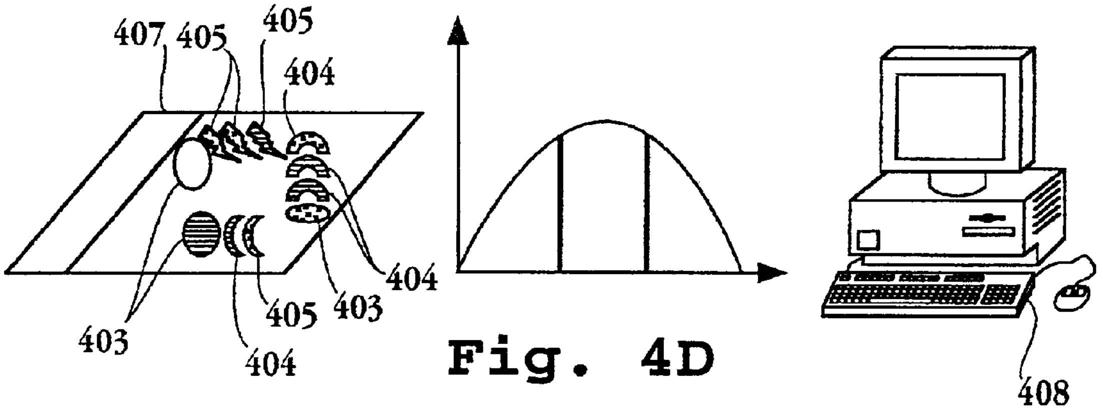
Figure 5A:
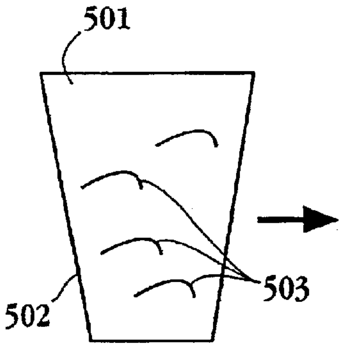
FIG. 5 depicts the detection of DNA after PCR.
Figure 5B:
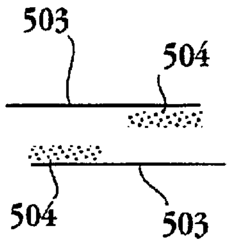
Figure 5C:
Figure 5D:
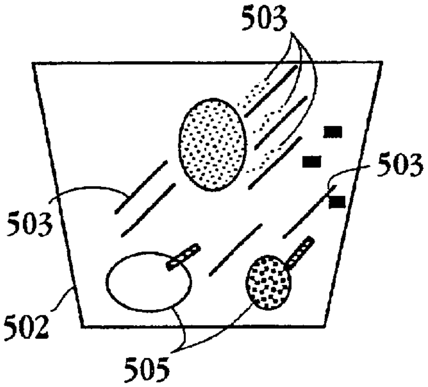
Figure 5E:
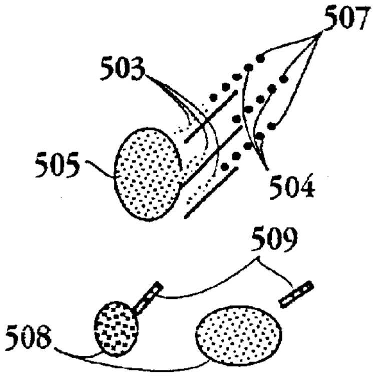
Figure 5F:
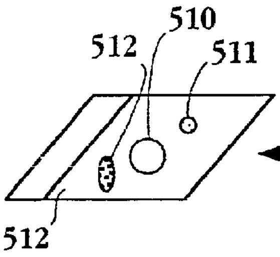
Figure 5G:
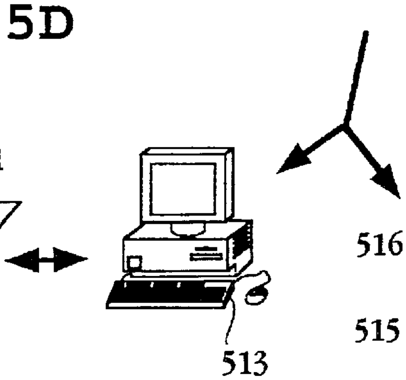
Figure 5H:
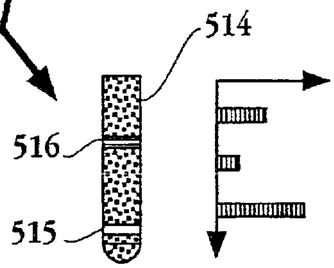

FIG. 3 depicts one preferred embodiment of using layered taggants as carriers. Sheet (301) comprising coding layers (302) is cut by cylinder micro-punch (303) into cylinders (304) allowing these to be imaged (deconvoluted) by flowing cylinders (304) through capillary tube (305) having an inside diameter slightly larger than cylinders (304) past color-sensitive detector (306) having viewing window (307) which is able to read the successive color layers in each carrier. In this way, the identity of each different carrier can be quickly established by scanning the flow of cylinders through the capillary tube.

In use, a composition containing up $M^N$ different coded carriers, each formed with a different surface-attached compound, for example, oligonucleotide, oligopeptide, or small organic compound, is reacted with a target, for example, receptor molecule, under conditions which lead to binding of the target to beads carrying compounds that bind specifically to the target. Preferably the target molecules are labeled, e.g., with a colored or fluorescent reporter. The carriers are then fed into a capillary flow tube, past a detector, where the carriers are first scanned for the presence of target binding. For those carriers that have bound target, a second scanning device then "decodes" the pattern of colors of the device, to identify the compound on the carrier according to its carrier code. It will be appreciated that other types of carriers, for example, cylindrical or rod-shaped carriers, that can be oriented in a capillary flow tube, and which can be encoded in a top-to-bottom fashion, e.g., with different layers having individually identifiable indicia, can be employed in the method. Thus, cylindrical carriers having layers of different fluorescent labels can be "decoded" in the same fashion. Alternatively, the carriers may have a magnetic layer or component that allows for magnetic separation of said carriers.

FIG. 4 depicts a method for comparative hybridization analysis. FIG. **4*a* depicts different coded carriers (401) being combined with different probe DNA (402) thus producing probe carriers (403). FIG. 4*b* depicts probe carriers (403) being combined with both labeled reference DNA (404) and labeled test DNA (405) in tube (406). FIG. 4*c* depicts the hybridization of labeled reference DNA (404) and labeled test DNA (405) with probe carriers (403). FIG. 4*d* depicts post-hybridization probe carriers (403) with bound DNAs (404) and (405) randomly distributed upon slide surface (407). FIG. 4*e* depicts the use of a computer based system (408) to identify DNAs (404) and (405) and determine the codes contained within probe carriers (403)**.

FIG. 5 depicts the detection of DNA after PCR. FIG. **5*a* depicts serum sample (501) containing viral DNA sequences (503) in tube (502). FIG. 5*b* depicts the addition of specific primers (504) at a concentration less than viral DNA sequences (503) concentration. PCR cycles are then run until most primers (504) are used. FIG. 5***d* depicts combining both carriers with specific primers (504) attached to coded carriers (505) such that individual carriers (505) contain only one type of specific primers (504) in tube (502) with a labeled nucleotide cocktail, not shown. Viral DNA sequences (503) are then hybridized to their related specific primers (504) attached to coded carriers (505). A polymerase fill in reaction or PCR is then performed to extend specific primers (504) attached to carriers (505) incorporating the labeled nucleotides not shown. Carriers (505) with unrelated primers attached do not extend or amplify and thus do not incorporate labeled nucleotides into specific primers (504) attached to carriers (505). FIG. 5*e* depicts the end result of specific primer (504) extension shown in FIG. 5*d*. In particular, labeled carrier (506) comprising coded carrier (505) having a related specific primer (504) and viral DNA sequence (503) and newly extended and labeled primer strand (507). Also shown are unlabeled carriers (508) bearing unrelated primers (509). FIG. 5*f* depicts the random distribution of both labeled (510) and unlabeled (511) carriers on slide (512). FIG. 5*g* depicts a computer used to determine and record active positions and coding data collected from the random array of carriers (505) depicted in FIG. 5*f*. FIG. 5*h* depicts an alternate means for analyzing labeled carrier by differential sedimentation or buoyant density gradient separation where labeled (510) and unlabeled (511) carriers are separated into several classes, (515) and (516) based on density which encodes the carrier, and examining which carriers are labeled.

Figures 6A, 6B, 6C, 6D, 6E:
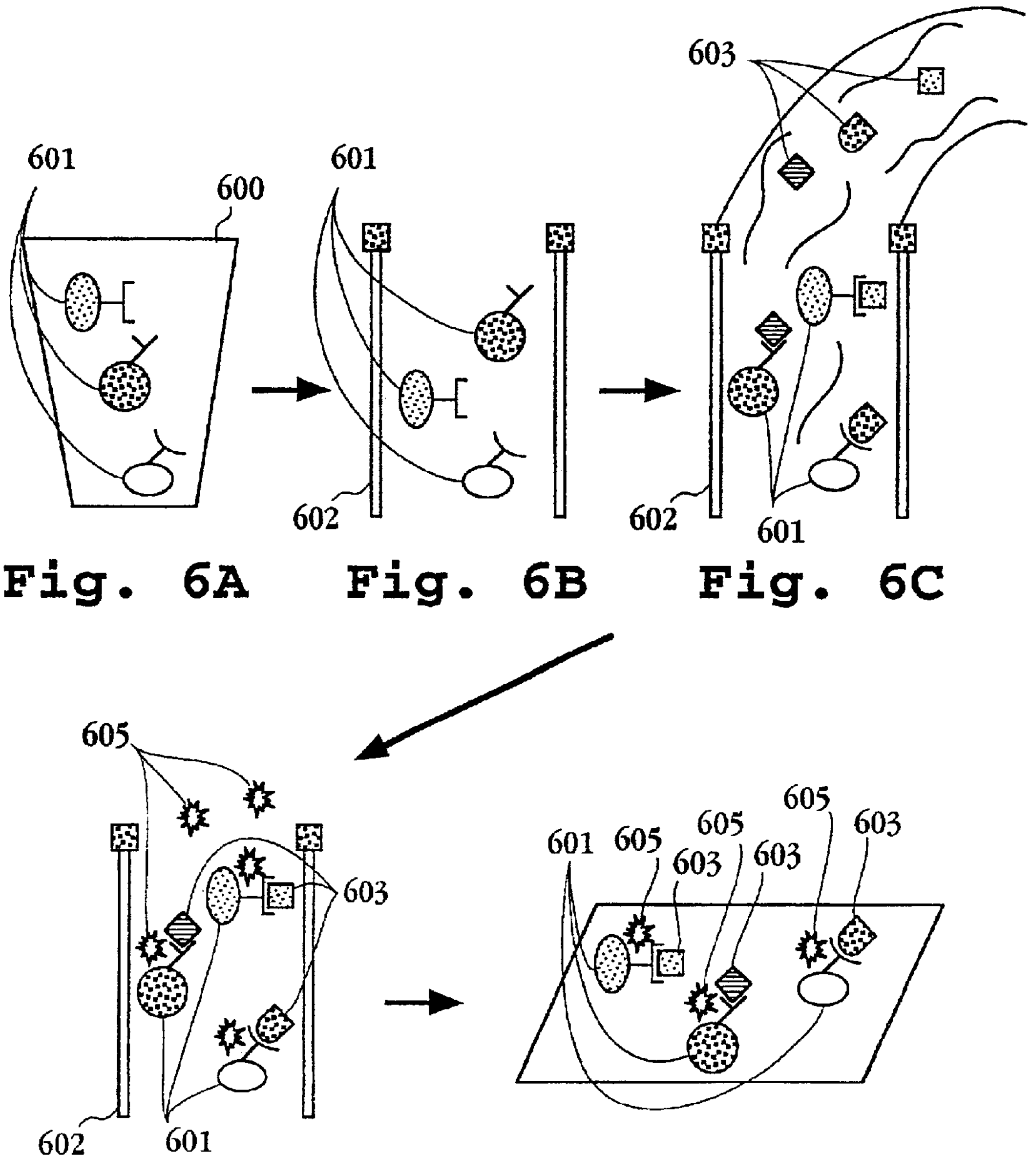
FIG. 6 depicts a method for specifically detecting and identifying different microorganisms suspended in a liquid medium.
Figure 7A:
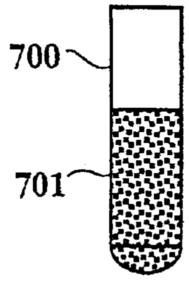
FIG. 7 depicts a method for measuring CD4/CD8 T cell ratios in blood.
Figure 7B:
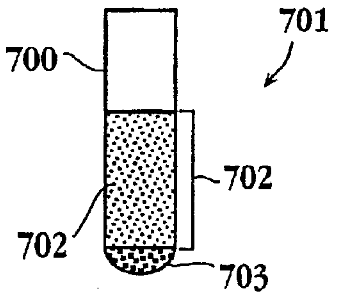
Figure 7C:
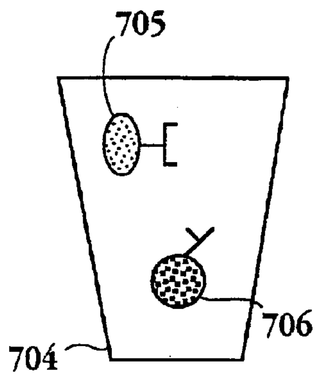
Figure 7D:
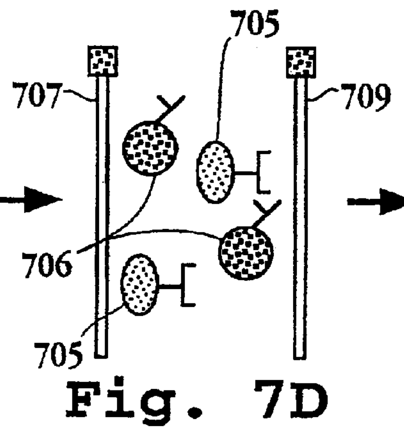
Figure 7E:
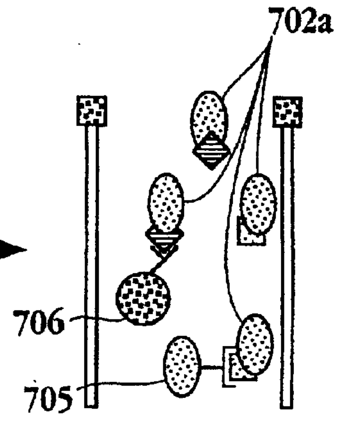
Figure 7F:
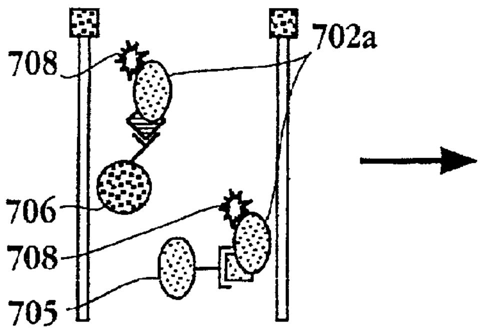
Figure 7G:
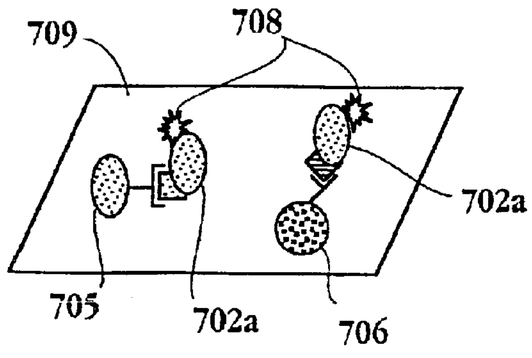

FIG. 6 depicts a method for specifically detecting and identifying different microorganisms (603) suspended in a liquid medium. FIG. 6*a* depicts different carriers (601) each coated with different capturing antibodies (601*a*) specific for one type of different microorganism (603). FIG. 6*b* depicts the placement of carriers (601) into column (602). Liquid medium source (604) containing microorganism (603) is supplied to column (603) and liquid medium (604*a*) is allowed to flow through column (602) and contact carriers (601). Microorganisms (603) contact and bind their respective, specific carrier (601). FIG. 6*d* depicts the excess addition of generic reporting molecule (605) that binds all microorganisms (603). Carrier (601) microorganism (603) and generic reporter molecule (605) are then randomly placed on surface (606) for analysis and code determination.

FIG. 7 depicts a method for measuring CD4/CD8 T cell ratios in blood. FIG. 7*a* depicts tube (700) containing whole blood sample (701). FIG. 7*b* depicts whole blood sample (701) after fractionation into WBC (702) and RBC (703) fractions. FIG. 7*c* depicts container (704) containing different carriers each displaying different capturing antibodies such that antiCD4 carrier (705) captures CD4 bearing cells, and antiCD8 carrier (706) captures only CD8 bearing cells. FIG. 7*d* depicts antiCD8 carriers (706) and antiCD4 carriers (705) placed into column (707). FIG. 7*f* depicts bound WBC cells (702*a*) bound to their respective antiCD4 carriers (705) and antiCD8 carriers (706) depending on which antigen is displayed on each WBC cells (702*a*), and generic detection molecule (708), such as a detectable antiDNA antibody, attached to each WBC cell (702*a*). FIG. 7*g* depicts carriers (705) and (706) randomly distributed onto surface (709) for detection and code determination.

Figures 8A, 8B, 8C, 8D, 8E:
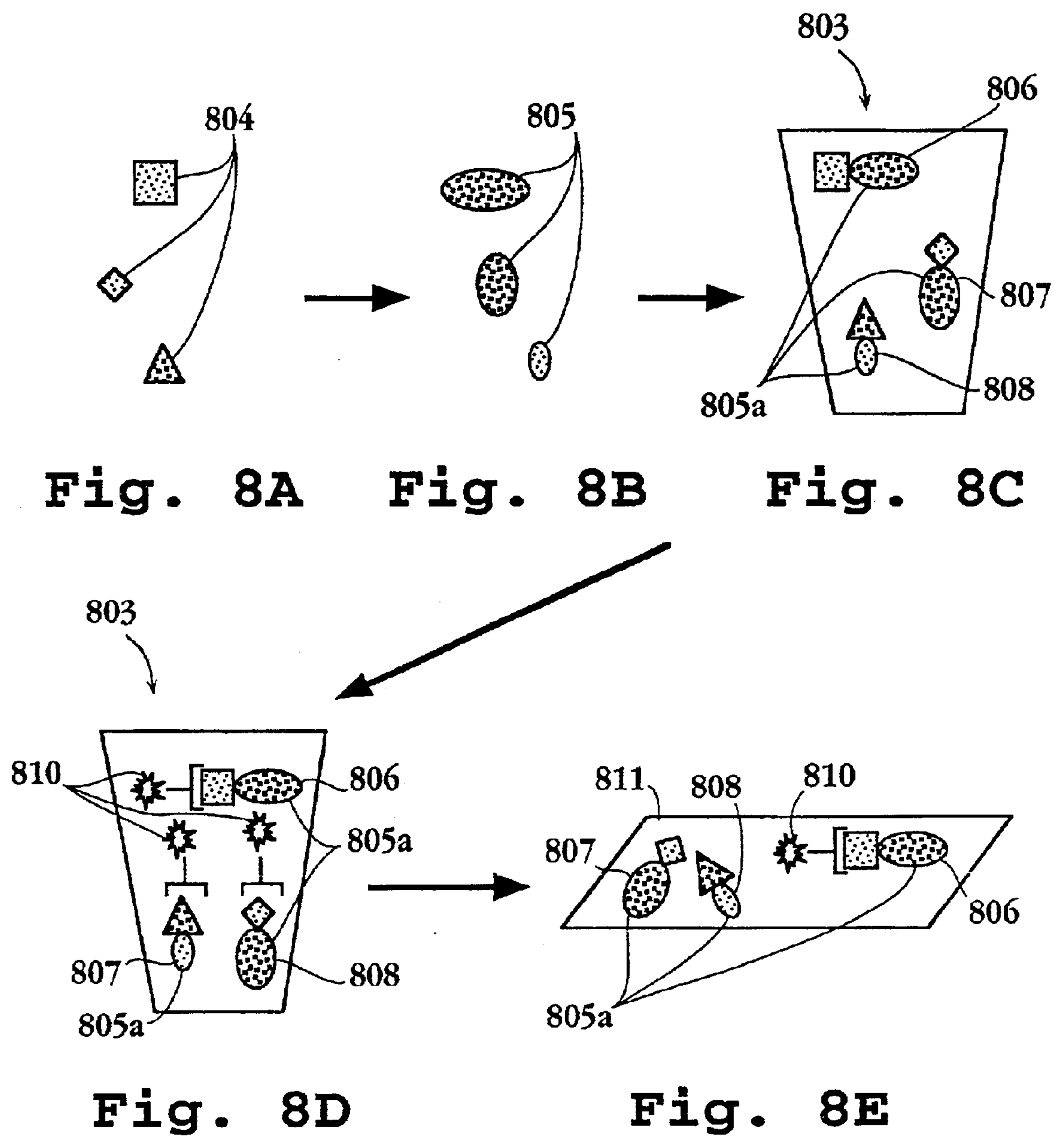
FIG. 8 depicts a method for screening synthetic molecular compound libraries for drug discovery.

FIG. 8 depicts a method for screening synthetic molecular compound libraries for drug discovery. FIG. 8*a* depicts ligands (804). FIG. 8*b* depicts coded carriers (805). Different coded carriers (805) are combined with different ligands (804) such that each distinct class of ligands (804) is combined with a distinct class of coded carriers (805) to form different carrier classes each having one compound as in class 1 carrier (806), class 2 carrier (807), and class 3 carrier (808). All carrier classes (805*a*) are combined into tube (803) as depicted in FIG. 8*c*. FIG. 8*d* depicts the addition of detectable target receptor (810) to all carrier classes (805*a*) in tube (803) so that target receptor (810) only combines with carrier class (806) and not carrier classes (807) or (808). FIG. 8*e* depicts the random placement of all carrier classes (805*a*) for detection and code determination. The method described in this paragraph may be practiced by either coating different classes of carriers with different ligands for screening against one receptor class, or conversely, coating different carrier classes with different receptor classes and screening them against one ligand class.

Figure 9:
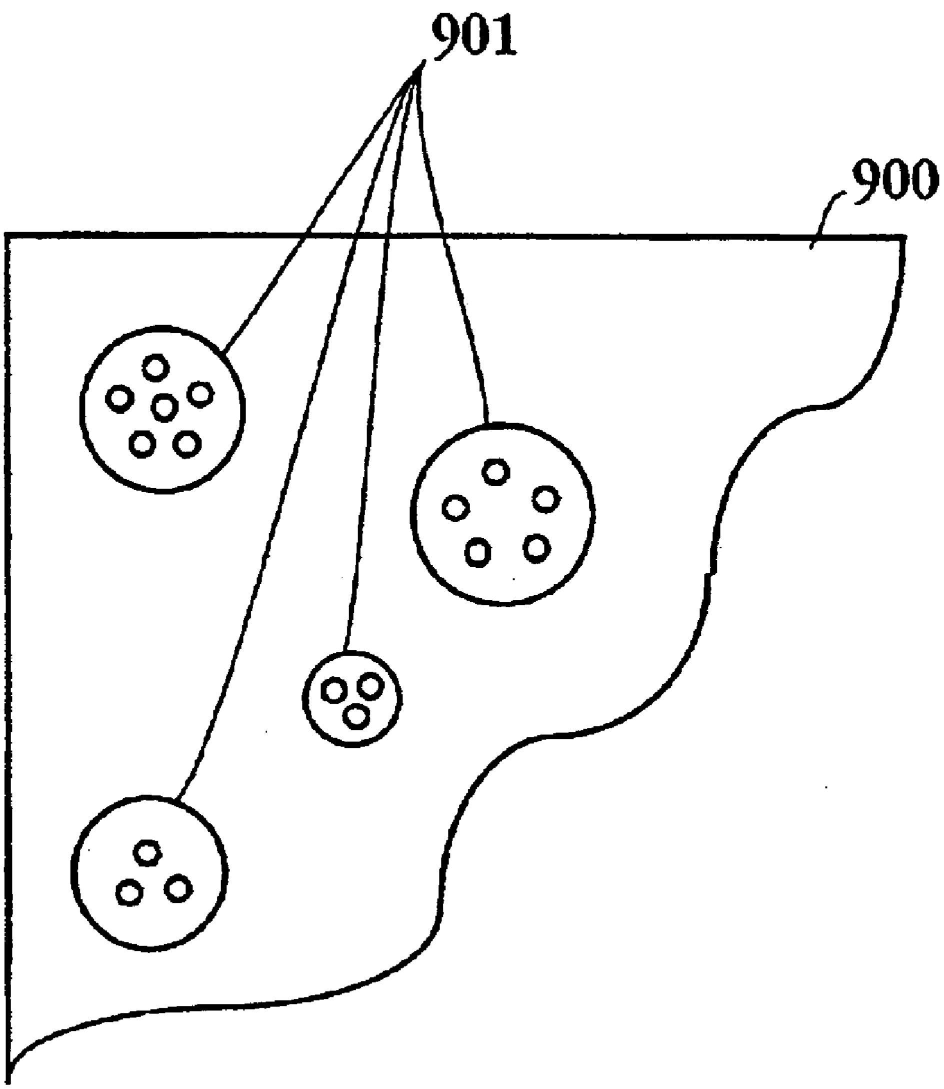
FIG. 9 depicts a surface with carriers distributed thereon.

FIG. 9 depicts surface (900) with carriers (901) distributed thereon.

Figure 10A:
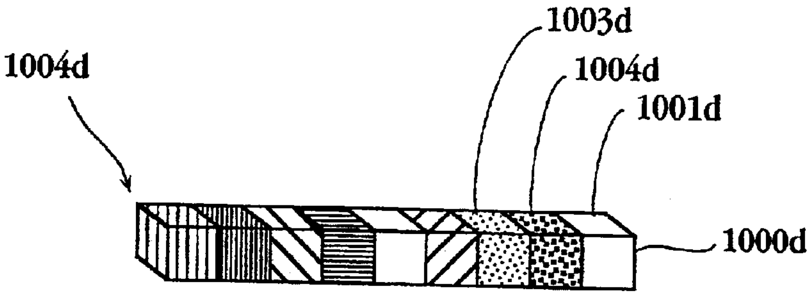
FIG. 10 depicts several different embodiments of taggants.
Figure 10B:
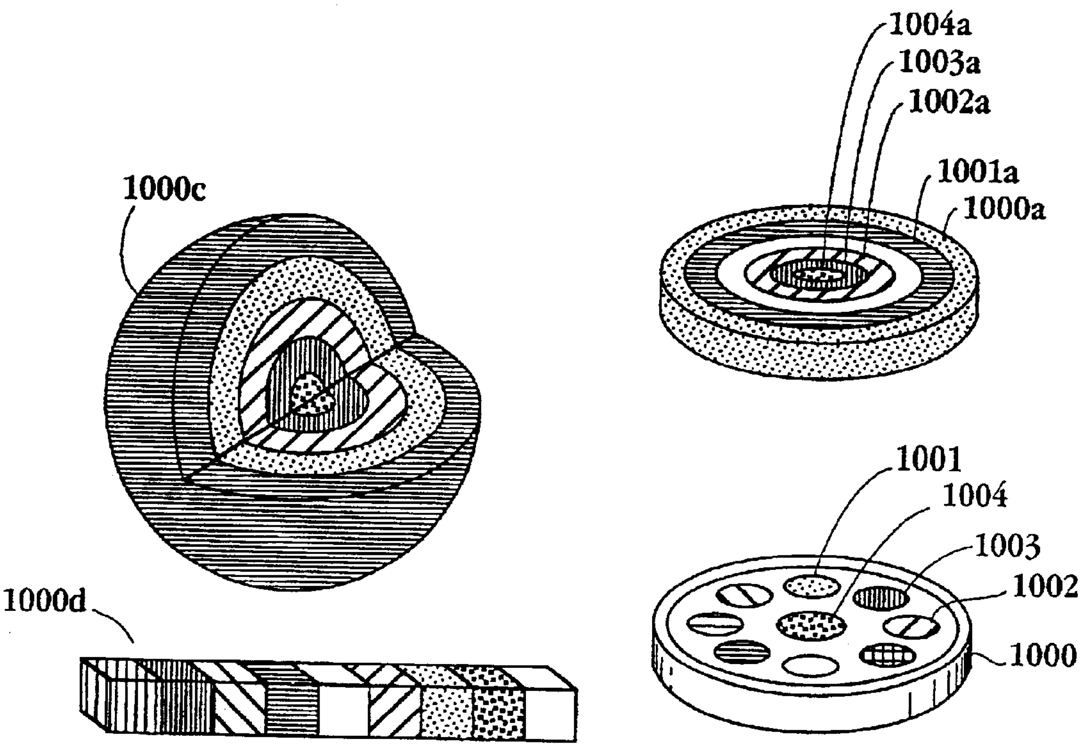

FIG. 10 depicts several different embodiments of taggants (1000, 1000*a*, 1000*b*, 1000*c*, 1000*d*) suitable for use as carriers. Taggant (1000) is made by bundling distinctive fibers without twining, and shearing off disks by cutting the bundle, typically after its diameter has been reduced by stretching the bundle longitudinally. Distinctive fibers (1001), (1002), may be combined with center alignment paramagnetic core (1004) and a position marker (1003). Position marker (1003) is used to establish the proper reading frame of taggant (1000). Each of the other embodiments shown follows a similar scheme. As can be seen, flat shapes provide excellent optical access to the code to facilitate code determination.

Figure 11:
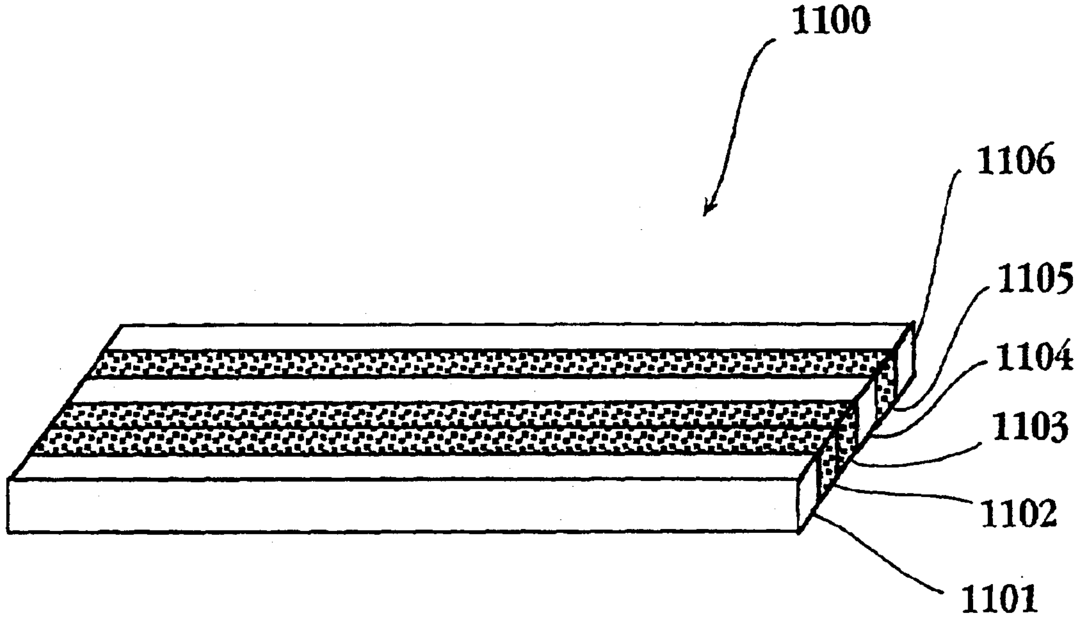
FIG. 11 depicts a fused glass fiber carrier.

FIG. 11 depicts a fused glass fiber coded carrier. Fused fiber carrier (1100) comprises a sandwich of fibers, attached to each other. The fibers (11001), (1002), (1003), (1004), (1005), and (1006) may be attached by bonding, fusing, heat fusion, gluing, or encasement by a sheath, such that the cross sectional arrangement of the fibers is fixed.

Figure 12:
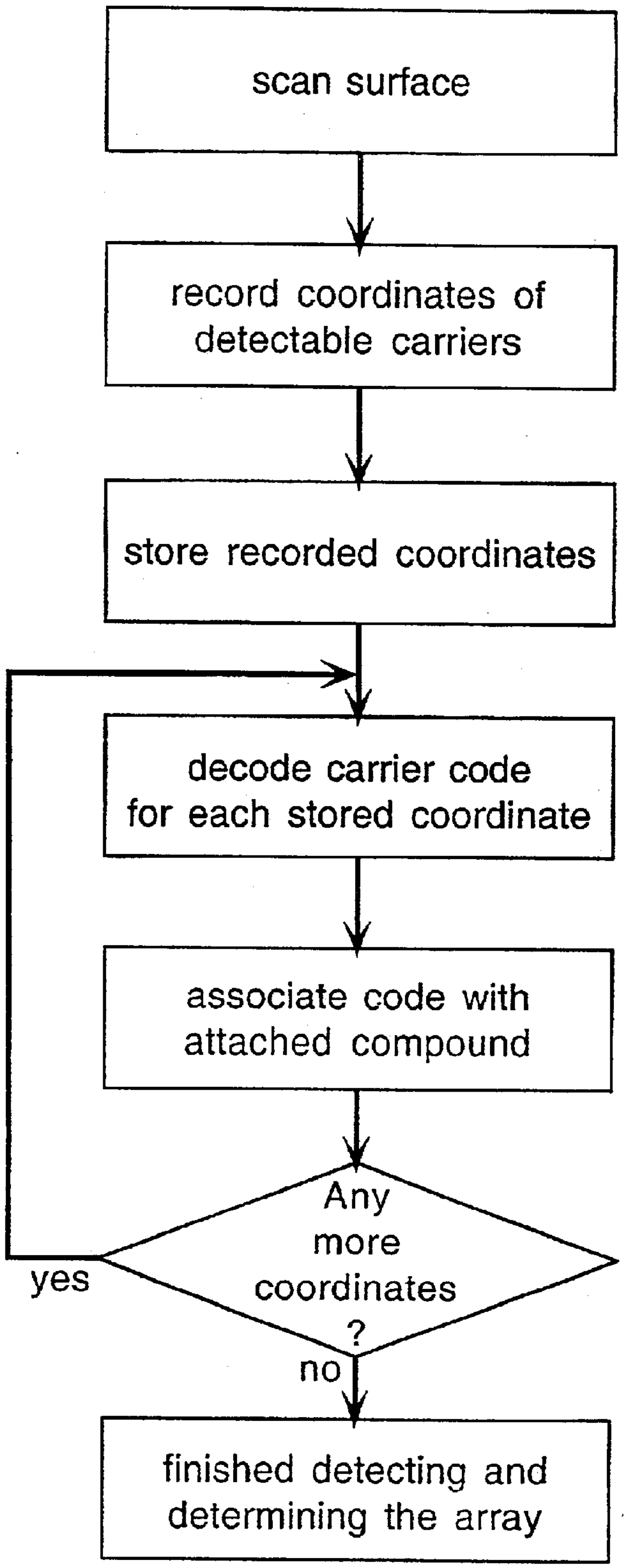
FIG. 12 depicts a method for using carriers.
Figure 13A:
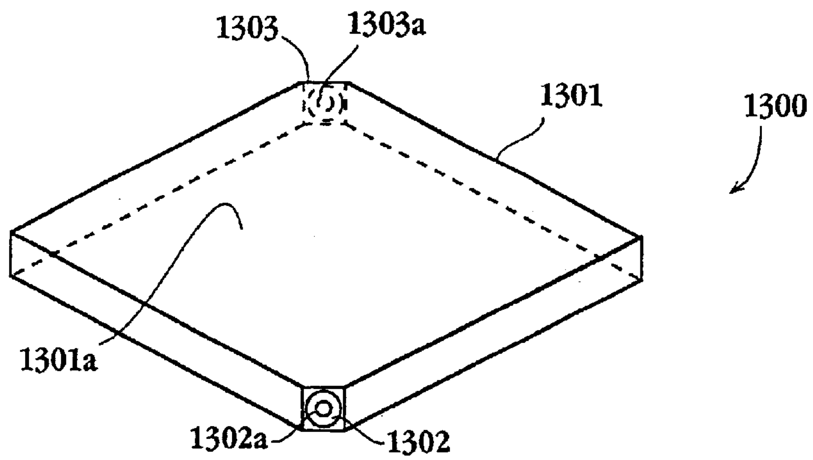
FIG. 13 depicts an array organizer.
Figure 13B:
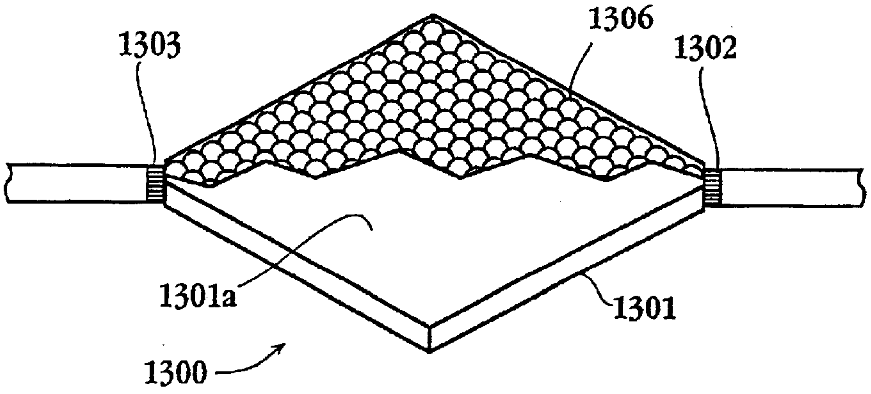
Figure 13C:
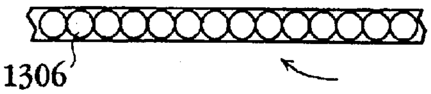
Figure 13C:
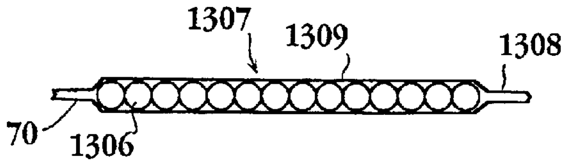
Figure 13E:
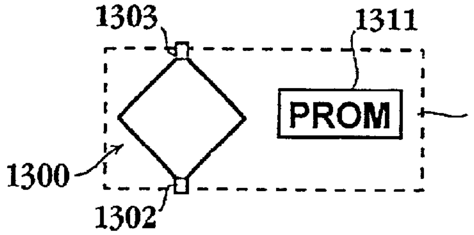

FIG. 12 depicts a method for analyzing active carriers and determining active carrier codes.

FIG. 13 depicts a carrier array fixedly organized in a structure. Fixed array (1300) contains carriers (1306) fixedly organized by the interior geometry of array organizer (1301) and the geometry of carriers (1306). FIG. 13*a* depicts array organizer (1301) used to form fixed array (1300). Array organizer (1301) has an inlet (1302) with inlet frit (1302*a*) and outlet (1303) with outlet frit (1303*a*). An exhaust port, not shown, may be included with array organizer (1301) for gas or fluid escape. Array organizer (1301) may provide flat viewing surface (1301*a*) or other surface such as a cylinder surface. FIG. 13*b* depicts carriers (1306) packed such that once carrier (1306) is assembled during manufacture, carriers (1306) cannot shift in position thus being fixedly organized. Frits (1302*a* and 1303*a*) prevent carriers (1306) from escaping from array organizer (1301). FIG. 13*c* depicts a cross sectional view of array organizer (1301) with an array of carriers (1306) organized therein. Depending on the shape of carriers (1306), very little dead volume exists in organized array (1300). For example, six sided disks having a top surface, a bottom surface, and six sides forming a hexagon, could compact with their top and bottom surfaces contacting array organizer (1301)'s top optical viewing window (1301*a*) or bottom optical viewing window (1301b) respectively, and where carrier (1306) sides would align to form a "honeycomb" arrangement, thus minimizing dead volume while maintaining maximum carrier (1306) fluidic contact. FIG. 13*d* depicts capillary carrier array (1307) having capillary shaped array organizer (1309) with carriers (1306) fixedly organized therein and maintained by capillary pinch points (1308) and (1310) such that carriers (1306) fixedly rest against one another thus minimizing dead volume. FIG. 13*e* depicts organized array (1300) fixedly attached to surface (1312) having memory device (1311) further attached to surface (1312).

The invention further provides for methods to measure one or more target-compound interactions. This can be done with the same image processing methods, e.g., correcting the background and calculating the integrated intensity. Reading of specimens produced according to the present invention can also be done, for example, on a microscope equipped with appropriate optics, camera and software.

Since the invention provides for many different types of carriers, different methods of carrier code identification are provided depending on the nature of the particular carrier's encoding properties. If carriers are beads of different size, the diameter of the beads can be estimated from the image of a field containing them in transmitted light, fluorescence, phase contrast or other microscope modalities. The most common way of acquiring a digital image at this time is by means of a CCD camera. Once the image field is obtained, it can be corrected for background variation and thus a threshold level set. Each connected set of pixels represents a carrier or bead. The area of such a set is the number of pixels, and from this area the diameter can be calculated. This is the simplest way of estimating the diameter. More accurate methods have been developed that give accuracy of a fraction of the pixel size, see generally Verbeek, et al., IEEE Transactions on pattern analysis and machine intelligence; 16(7): 726–733 (1994), and van Vliet, et al., Proc. IEEE Instrumentation a and measurement technology conf. IMTC94, Hamamatsu, Japan, May 10–12, 1994, pages 1357–1360, each of which is herein incorporated in their entirety by reference.

A high degree of measurement accuracy can be achieved by developing a theoretical model of image intensity distribution produced by each class of carriers and fitting it to the actually observed images.

$$\text{Image Intensity}=f(x,y|P),$$

where: x, y are pixel coordinates relative to the center of the carrier, P is the parameter vector, which can consist, for example, of the size parameter and the brightness parameter.

These functions can be constructed because the carrier classes, the microscope optics, and the image acquisition system are known and can be characterized analytically. The approximation of the theoretical image intensity to the observed image intensity can be done by the least squares method, see generally Press, et al., "Numerical Recipes in C: The art of scientific computing", Cambridge Univ. Press, Cambridge (1988), herein incorporated in its entirety by reference. The result of this approximation is a parameter vector, which gives the best fit. The values of parameters determine the class to which the carrier belongs. In the example of beads of different sizes the accuracy of measurement and the accuracy of manufacturing of the beads determine the possible number of classes that can be allocated to the size feature in a certain practical size range.

If carriers are different by color, a set of images, corresponding to different spectral bands, may be acquired. A combination of these images can be used to produce and analyze the mask of the beads as described in the previous paragraphs. For each bead mask relative image values can be determined in all spectral images. Each bead color will generate a characteristic set of these values, which can be used to identify them.

There are several commercially available image processing packages that could be used to perform all required operations for the described method, for example, Image Pro Plus by Media Cybernetics, Aphelion by Amerinex Applied Imaging, and IPLab by Signal Analytics Corp.

The invention has many facets, each of which may have many forms that may be combined to form numerous permutations of the invention. For example, carrier structure may play several different roles, compounds may be attached in differing ways to carriers, screening may occur before or after array determination, and arrays may either be preformed by the manufacturer with determination occurring by the manufacturer or the end user. Accordingly, a detailed examination of each step is provided with exemplary permutations presented where appropriate. Permutations included in this specification are merely illustrative and are not to be considered limiting of the scope of the instant invention.

The structure of a carrier may provide several key features. For example, the geometry of a carrier may serve as coding indicia. Carriers would then be distinguished by their appearance or by physical differences caused by their shape. The shape of a carrier may affect the carrier's hydrodynamic character in a way that distinguished each species of carrier from one another. Shape may also play a role in how a carrier displays itself. Cylinders of stacked laminates may be used in conjunction with a tube reader. The cylinders self-orient as they enter the tube reader thus presenting their band pattern as they pass a detector. Hemispheres will settle in a fluid with their flat surface upwards if the hemisphere is weighted on the apex of the spherical side. Disks are preferred because they orient with either disk surface facing upwards. This is helpful when encoding comprises combining strands of colored fibers into a bundle that is later sliced to form disks.

Carrier orientation is often important when optical code determinations are made. Coding regions must be exposed in a direction suitable for interrogation. As discussed above, orientation may be specified by physical properties of the carriers. Orientation may be specified by carrier shape, but it may also be specified by weight, or buoyancy. Carriers may further orient themselves by the application of an external force aside from gravity. For example, carriers may have a para-magnetic quality such that when they are in the presence of a sufficiently strong magnetic field, they will align themselves accordingly. Carriers may further demonstrate dielectric potential such that carriers may be daisy chained by the application of a dielectophoretic alternating current field.

The invention provides for encoded carriers. Coding may be a determinable property such as spatially distinct indicia, temporally distinct indicia, and functionally distinct indicia. Spatially distinct indicia include any material, or combination of materials that can produce a discernable pattern. For example, a carrier may comprise a sandwich of individually discernable layers. Layers may differ in color, refractive index, refractivity, shade, or texture. So long as the different materials used for layers have distinguishing character that is detectable, such different materials may be used as coding indicia. Patterns may also be formed in microchips by photolithography, or onto films such as with microfilm technology. For example, shapes may be combined with colors to improve diversity. Available indicia from one class may be combined with indicia from other classes to further broaden the coding vocabulary. Layers may, for example, be formed as sandwiches, ribbons, twines, ropes, concentric spheres, cables, strands, cylinders, cubes, disks, pyramids, or combinations of these embodiments.

Indicia may be temporally distinct, that is dynamic rather than static as described above. Temporal coding may arise by short pulse excitation of fluorophores having different hysteresis, that is, individual fluorophores will emit light back at different times for different durations. Any electromagnetically-induced effect can act as coding indicia if it either responds to a specific impulse, or produces a specific response.

Indicia may also be functionally distinct. As discussed above, carriers may be discerned based on their electrophoretic properties. Such properties may be dictated by either electrical characteristics, isoelectrical characteristics based on pH, and physical or hydrodynamic properties, or a combination of these attributes. Buoyant density may be used as well as sedimentation velocity. Molecular recognition may be used by methods such as agglutination and surface labeling. The latter may further impart upon a carrier some other attribute such as color or density if, for example, a colloidal gold conjugate is used.

If DNA is used as indicia, encoding can be done by varying the number of bases between a set of constant PCR primers. Performing PCR with appropriate primers would then yield DNA of a particular length corresponding to a particular carrier class. PAGE, CE, or HPLC could then be used to ascertain carrier DNA lengths. By using different primer sets on a subset of the carriers, greater diversity could be realized, however at the expense of running additional PCR reactions. Once the DNA lengths are determined, the carrier identity, and thus the compound carried on it, can be determined.

Carriers may be manufactured by many different methods. For example, disk carriers may combine or bundle together several different strand materials. Strands may differ by color, response to chemical treatment, refraction, shade, physical property including magnetism, or by composition. Bundled strands may then be pulled and stretched to reduce the diameter of the bundle. Heat may be applied to facilitate this process. Once a desired diameter is attained, the bundles may then be sliced, sheared, or abraded to produce microscopic disks or cylinders. Longer segments may be cut to produce rods that may be read by rotating the rod while observing the circumference of the rod-cylinder. Particularly preferred methods are described in U.S. Pat. Nos. 4,390,452; 4,329,393; 4,053,433; 3,897,284; and 4,640,035, all of which are entirely incorporated herein by reference.

Color-coded taggants can also be manufactured according to the methods described in U.S. Pat. No. 4,640,035. These carriers are manufactured as thin transverse sections of an assembly of elongated elements (e.g. fibers) of different colors forming a transversal united structure. After sectioning such structure the resulting plurality of distinguishable areas in each carrier (and their relative location) provide a coding element. Furthermore the assembly can be produced by combining preexisting filaments or by extrusion through a die and drawn down to a desired size before sectioning.

In use, a composition containing up to $M^N$ different coded carriers, each formed with a different surface-attached compound, e.g., oligonucleotide, oligopeptide, or small organic compound, is reacted with a target, e.g., receptor molecule, under conditions which lead to specific binding of the target to carriers carrying the appropriate compound(s). Preferably the target molecules are labeled, e.g., with a colored or fluorescent reporter. The carriers are then fed into a capillary flow tube, past a detector, where the carriers are scanned for the presence and amount of target binding, and the color pattern is decoded and the compound on the carrier identified according to its code. It will be appreciated that other types of carriers, e.g., cylindrical or rod-shaped carriers, that can be oriented in a capillary flow tube, and which can be encoded in a top-to-bottom fashion, or in spiral fashion, e.g., with different layers having individually identifiable indicia, can be employed in the method. Thus, cylindrical, or elongated carriers having layers of different fluorescent labels can be "decoded" in the same fashion. Alternatively, the carriers may have a magnetic layer or component that allows for the magnetic separation or orientation of said carriers.

More generally, in use, the method of the invention is designed for detecting one or more target molecules capable of binding specifically to one or more different, known library compounds. In practicing the detection method, the target is contacted with the library composition of the invention, that is a chemical-library composition composed of (i) a plurality of coded carriers, each having N>1 specified code positions and one of M>1 detectable indicia at each code position, such that each carrier can be identified by one of up to $M^N$ different code combinations, and (ii) a different known library compound carried on each different-combination carrier. The contacting is carried out under conditions in which the target molecules can bind specifically to known library compounds. For example, in the case of polynucleotide target binding or oligonucleotide-coated carriers, the contacting is carried out under conditions in which the target can bind by hybridization to complementary-strand oligonucleotides on the carriers.

The carriers, some of which have bound target, are then distributed for carrier decoding. In the example described above, cylindrical, or elongated carriers are distributed for carrier flow through a capillary flow path. Alternatively, the carriers can be distributed on a glass slide to be examined or scanned, e.g., by light microscopy or raster scanning, according to methods employed for DNA-chip scanning.

The scanning serves the dual purpose of decoding the carriers, and thus identifying the specific compound carried on the carrier, and to assess the amount of bound target on the carriers. The target may be detectable in native form, or may be labeled, e.g., by fluorescent label, for detection.

It will be appreciated that this method can be used in any application currently employing position-addressable microarrays of compounds, e.g., oligonucleotides, but in a much simpler, more flexible, less expensive format.

Finally, considering the construction or preparation of the composition of the invention, this is done, in the most general case placing into each of a plurality of a separate reaction vessels, carriers having a selected one of a plurality of detectable code combinations, each defined by one of N>1 specified code positions and one of M>1 detectable indicia at each code position, such that the carriers in any vessel all have one of up to $M^N$ different code combinations. Thus, for example, in forming an $M^N$ size oligonucleotide library, carriers containing one of the $M^N$ codes are placed into each of one of $M^N$ separate reaction vessels. The carriers are prepared according to known methods to act as the support surface for stepwise solid-phase synthesis. Thus, for example, the carriers may include a linker and suitable terminal chemical group for attachment of an initial protected nucleotide. Furthermore, a plurality of different linkers may be situated on a carrier either as a whole, or in specific locations where each location has a different linker on it. Different linkers may differ in functionality of reactions conditions. A combination of such linkers enable orthogonal coupling of compounds to a carrier. Moreover, a carrier may be combined with a plurality of compounds to create a multicompound carrier. A preferred example is combining fluorophores with cleavable quenchers, where cleavage occurs as a result of a target event. Quencher release then permits the fluorophore to detectably fluoresce. Such compounds, molecules and chemistries are known by thus skilled in the art. Therefore, each reaction vessel is subjected to steps for forming a selected oligomer sequence associated with the known carrier code in each vessel. This process is repeated until the compound associated with each carrier has been formed on the carrier. Alternatively, the compounds to be attached to each carrier can be prepared independent of the carrier, and attached by covalent coupling, after final compound synthesis.

Once the $M^N$ different carriers are formed in this manner, the carriers may be mixed in a desired fashion, e.g., equal numbers or weights of carriers from each vessel to form a library composition containing all or a selected subset of the $M^N$ different carriers, each carrying a different known compound.

In one additional and attractive embodiment of the invention, the carriers in the chemical library are prepared by attaching to them DNA probes containing their own signaling mechanism (e.g.—"molecular beacons") such that only in the presence of the specific target molecule a fluorescent signal is emitted. This allows sensitive and specific reading of the signal and an excellent signal-to-noise ratio. This is particularly useful in applications associated with single nucleotide polymorphisms where the differences between genes are small.

Spheres or beads may serve as carriers. Beads may be discernable by size, density, granularity, refractive index, color, fluorescence, or may contain yet another carrier or carriers that are further discernable. Beads may contain sub-populations of other, smaller beads distinguishable by color or other optical or physical features. Beads may be produced by a variety of methods including ultrasonic fluidic drop formation. Such methods produce exceedingly uniform bead diameters and spherical shape. Drop size is highly controllable so that preparation of a library of different sized carriers is possible. Beads can also be formed in a non-uniform manner, and then later sized by passing through a descending series of mesh screens. Polymer solutions used to form beads may themselves contain beads or particles, or combinations of each, smaller than the to-be-formed bead diameter. Examples of beads and particles can be found in Bang's bead catalog, Flow Cytometry Standards catalog, and Molecular Probes catalog, each of which is herein incorporated by reference.

A particularly preferred carrier is formed from a layered sandwich code. Such layered sandwiches may be formed by bonding film layers together to form a pattern in cross section. Like strands, film layers may differ from one another by chemical, optical, or electrical properties. Chemical differences may include differential reactivity, isotopic, see for example U.S. Pat. No. 5,760,394, herein incorporated in its entirety by reference. Indicia may also include radioisotopic differences and resistance to chemical attack. Optical differences may include calorimetric, reflective, granularity, polarization, and optical index. Electrical differences may include dielectric properties, where the sandwich yields a particular capacitance as a result of serially forming a capacitor sandwich, or the difference may be in resistance where each layer has a unique resistive value that can be combined to form a total and distinct resistance.

Films may be used for carriers. In particular, U.S. Pat. No. 4,390,452 describes the use of microfilm or microfiche disks or fragments, photographically imprinted with a code to create taggants and is herein incorporated in its entirety by reference. Films may further be layered upon an orienting layer to aid in orienting the image for visualization. Films may also be imprinted by inkjet, photolithographic, electrostatic, or xerographic methods.

Structures may also be used as carriers. A given structure may serve as a support for a coding scheme as in the case of films. A structure may also serve as the coding source or indicia by etching with photolithographic methods to create an optical pattern. Combination approaches may include a layer sandwich punched out into discernable shapes. Differing coding structures may also be produced by extrusion, molding, spray formation, electrospray deposition, vapor deposition, machining, punching, or may be naturally diverse, for example, particular species of diatoms. Structure differences may also occur at the atomic or polymeric level, for example, as with "bucky balls."

Carriers may be supplied to end users in a variety of ways. For example, arrays or libraries of compounds coupled to encoded carriers may be supplied either unblended or preblended. Moreover, blended arrays may further be allocated or individually formed as single or non or minimally redundant arrays. Naked or compoundless coded carriers may also be supplied so that the end user may couple their compounds to carrier populations with a particular code, and combine different compound carriers to form a custom library or array. Any format described here may be sold by a manufacturer as a kit including reagents and instructions for making an array.

Compounds may be attached to carriers in a variety of ways. Compounds may be synthesized in place, typically on some linker. Parallel synthesis may speed up the process. Many commercially available synthesizers may be used to synthesize compounds onto carriers. Compounds may also be attached to reactive linkers, or by adsorption. This permits both natural product and synthetic compounds to be linked to carriers. Large molecular structures such a receptors and enzymes may also be attached either by covalent, adsorptive, or binding reactions. Binding reactions may include, for example, biotin-streptavidin, or biotin-BirA interactions. Receptors bound to carriers are well suited for soluble ligand binding studies. In particular, if a chemical or photocleavable linker is used to attach a compound to a carrier, and such a compound carrier is further combined with other carriers displaying receptors for which they too encode, a dual matrix of compounds and receptors or targets may be combined and analyzed. Analysis may be performed by looking for displacement of an already bound, fluorescent ligand from each receptor. If a nearby compound carrier so happens to be near a corresponding target receptor carrier, fluorescence will be lost on that receptor carrier. Placing a single compound carrier into an individual well containing a plurality of different receptor carriers may further enhance this assay format. Welless formats may use anti-convectancts such as agar or alginate to help limit diffusion.

Arrays may be physically retained to geographically fix the position of coded carriers. This is useful if the array is determined before contacting it with a target or analyte. A manufacturer may organize an array, determine what compound is at each position, and then embed that information into the array, or closely associate or attach the information to the array. A programmable read only memory semiconductor may be "burned in" with the compound coordinates for later look-up by an end user array scanning device. The end user would then add analyte, react and scan the array for active regions, where then a computer could correlate the scan data to the supplied ROM coordinate data to recreate an array. Organized arrays may also be identified by a serial number, perhaps in bar code format, that links the organized array to a data set held remotely to the organized array, for example, on a CD ROM. This would enable a manufacturer to sell lots of predetermined organized arrays linked to custom CD ROMS by bar codes, where the end user's scanning device would utilize coordinate information for each organized array stored on the CD ROM for correlating active regions within organized arrays to particular compounds.

Carrier shape may influence how an array is formed. For example, spheres naturally form a compact two-dimensional array if they have a different buoyant density then the medium, which they are suspended in. If the spheres are denser than the medium, the spheres will settle on the bottom of the medium, and if the medium is denser, the spheres will float. Either way, the spheres will settle, up or down, and form an array. Assuming that there are just enough spheres to create a monolayer of spheres tightly packed together, each sphere in the array will become relatively fixed in its position. Spheres allow for relatively simple array formation at high density. Other shapes may be used. For example, rectangular blocks may be used easily if they settle, on average, with enough space between so as to avoid stacking. Those carriers that do stack may be dislodged by mechanical agitation. By adding mechanical energy to the system, a higher degree of organization may be achieved. For example, the rectangular carrier described above may further be organized by tilting the settling plane to cause the carriers to slide up against one another. Further order may be realized by vibrating the plane to cause the carriers to further fit together. One skilled in the art would appreciate that many other shapes would create well-organized, compact arrays. In particular, hexagonal "disks" would compact nicely in to a honeycomb like matrix, well suited for later optical analysis. This approach may be used with disks, polygons, cubes, triangles, octagons, and the like. Particularly useful is a shape with a flat "viewing surface" that would self-orient such that all carriers in an array would settle with the viewing surfaces facing in one direction. Again, disks with one or more sides and at least one flat surface are ideal. As discussed above, weight distribution within the carrier may also facilitate orientation.

Arrays may be packaged in chambers that not only orient the carriers, but also make the carriers conveniently accessible to solvents and optical interrogation. For example, a planar diamond shaped container may be sealed on both faces with fluid input and output ports located distal from one another. Such a chamber would readily expose all carriers to solvents, in particular analyte solvents, by pumping in such solvent, with the output serving as a purge port. Washing is done by further flowing solvents across the chamber, thus contacting and washing each carrier. This arrangement is particularly suitable to automation.

Tubes, such as capillary tubes, may also be used to organize carriers. Tubes may be used to positionally fix carriers or to transiently align carriers for interrogation. In the former, for example, cylinder stacked carriers may be settled into a capillary and fixed into position by slightly pinching the capillary at each end. Fluids could then be perfused through the capillary to expose the carriers to analyte containing solvents. The capillary containing fixed carriers could then be interrogated by passing the capillary across a scanner. Alternatively, the cylinder carriers could be pumped through the capillary to orient and align the carrier with an interrogating window situated along the capillary path. In either case, cylinders can be introduced into the capillary by many methods, for example, by funneling the cylinders while they are suspended in a fluid matrix. Electrically polarized carriers could be suspended in an electrolyte fluid and electrophoretically induced to enter the capillary from the suspension solvent. Dielectrophoresis may also be used to "daisy chain" the carriers in a particular orientation. Combining paramagnetic material with a carrier would allow external magnetic fields to induce order amongst the carriers.

Arrays may be organized in different ways during their use depending on the stage of the array analysis. As described above, arrays may be organized before, during or after they are exposed to an analyte. Carriers within an array may be subdivided based on each carrier's response to an analyte. Thus, analyte reactive carriers may be concentrated such that all isolated carriers within that class exhibit a positive response. This separation serves to minimize the amount of code interrogation that must be performed. Response based separation is ideal for coding schemes or large arrays that may require an interrogation time duration not suitable for interrogating an entire array.

Arrays may be contacted with analytes and other solvents before, during or after organization. A simple method provides for contacting the array with an analyte in a standard reaction tube, performing all necessary steps such as washing in that tube, and then dumping the array onto a petri dish or slide surface for microscopic or other optical interrogation. Many organized array formats, such as capillaries and other chambers that provide fluid inlet and outlet ports, are ideal for exposing and washing arrays by robotic or other automated means. In essence, these chambers function like a chromatography column. Accordingly, tube diameters greater than two times the minimum diameter of a carrier may function well for contacting carriers with various solutions including analytes solutions. If the tubes are packed loosely, they may be vortexed to further contact the carriers with solutions. Column arrays are ideal for passing voluminous analytes such as drinking water microbial analysis. The carriers may then be analyzed by disbursing them onto a dish or slide surface, or by other means such as flow cytometry.

Arrays may be screened or analyzed before, during, or after the carrier identities are determined. Methods for screening generally involve providing a library of compounds on discretely coded carriers, contacting the carriers with an analyte potentially containing a target analyte corresponding to a carrier bound compound, allowing any target molecules to bind their respective compounds, detecting target molecules that may have interacted with their corresponding compounds, and determining carrier codes for at least the carriers with targets bound. The last two steps are interchangeable if all of the carrier identities are determined prior to detecting target-compound interactions.

A particularly useful method for using coded carriers employs flow cytometry analysis. Here, the user may contact an analyte with an array in a standard reaction vessel such as a test tube. After completing steps necessary to realize an optically discernable result on a carrier surface, the carriers may then be fed into a flow cytometer for analysis and separation. Analytical methods that may be adapted for use with coded carriers are described in detail in the Becton Dickenson FACStar Plus User's manual, herein incorporated in its entirety by reference. Analysis for target-compound interaction may result in sorting of "positives" from "negatives" where then carrier codes are later determined by additional flow cytometry, described below, or by placing the positives in a separate chamber or on a separate surface for optical analysis. A cell sorter is ideal for arranging carriers onto a grid for other analysis.

A particularly preferred method of using flow cytometry is to simultaneously, or near-simultaneously interrogate carriers for both target-compound interactions and carrier code identity. This may be done, for example, by using the optics of a flow cytometer to distinguish between different optical characteristics emanating from each component such as target-compound and carrier code optical characteristics. For example, Target-compound interactions may result in the binding of a FITC conjugate to the carrier. Using the blue output of the light source, typically a blue line of a laser, FITC is excited resulting in a green light emission. Thus, positive target-compound interactions fluoresce as green light. The green light is then detected by an optical detector tuned to respond to green light only. Carrier codes, on the other hand, may have several different color emissions as indicia. Such output may be analyzed as a composite, which is then used to reconstruct the carrier code by comparison of the composite spectra with a set of predetermined spectra. Problems may arise in that spectral analysis of the entire carrier may be confused by light coupling between different fluorescing components of the carrier code. To avoid this problem, the invention further provides for separating each fluorescing layer of the layered carriers with an opaque layer to prevent optical coupling. The result is that optical coupling is minimized and more predictable and optically discernable fluorescent outputs are realized. Using more than one laser to interrogate a carrier may further enhance this method. Many flow cytometers permit the use of multiple lasers to interrogate carriers suspended in the cytometer's fluid stream. The use of additional lasers set for different color outputs enhances signal separation when carriers are coded such that each fluorescent code layer is separated by an opaque layer. Since fluorophores that excite at shorter wavelengths are not optically coupled to fluorophores that excite at longer wavelengths, light emission of the longer wavelength fluorophore is minimized when shorter wavelength light is used to excite the shorter wavelength fluorophore because wavelength shifted light from the shorter wavelength fluorophore does not "spill over" to the longer wavelength fluorophore thus causing it to excite as well. Without optical separation between fluorophore code components, excitation of a higher wavelength fluorophore causes that fluorophore to emit lower wavelength light that then inadvertently excites another yet lower wavelength fluorophore to excite thus causing that lower wavelength fluorophore to emit a still yet lower wavelength of light. This greatly limits the number of discernable codes that a set of fluorophore indicia may provide. Optical partitioning, as described above, greatly reduces this "crosstalk" effect.

Carrier orientation during flow cytometry interrogation may be achieved by several methods. Shape, such as a cylindrical shape, may be used to orient a carrier in a fluid stream. Flow cytometry often uses two fluid systems to create a fluid stream for interrogation. A smaller diameter carrier-containing stream may be coaxially positioned within a larger diameter "sheath" stream. The flow rate of each stream may be differentiated to create eddy currents at the interface between the two sheaths. These eddy currents can produce a "riffling" effect to maintain cylinder orientation after ejection from a nozzle orifice. In another embodiment, paramagnetic material placed at one end of the carrier cylinder may be magnetically induced to orient the carrier in one direction as it traverses the cytometer's interrogation window. Each of these methods may be used to best orient a layered carrier, especially optically partitioned carriers. Translucent layering may also be used, especially for fluorophore film layers, to permit light entry and emission from several sides of a carrier. Interrogation may also be realized by illuminating and observing the same side of a carrier, illuminating from one side and observing from the opposite side of the carrier, or illuminating one side of a carrier and observing an adjacent side of the carrier.

Flow cytometry can measure several different aspects of a carrier simultaneously or near-simultaneously. For example, forward scattered light, FSC, indicates generally carrier size. Side scattered light, SSC, can indicate degree of granularity. Light scatter is light that is not "ballistic" with respect to the source, typically light not within the normal, undisturbed path of the collimated light source such as a laser. Both FSC and SSC light are measured at the same wavelength as the light source so as to distinguish such sources from fluorescent light emissions. Fluorescent emissions are usually distinguished by optically filtering with band pass, or combination of long and short pass, filters. Each fluorescent band detected is given a sequential identifier such as FL1 and FL2. Given the wide variety of information that a flow cytometer can gather from interrogating a carrier, such variety may deliberately be used as coding indicia.

As discussed above, carriers may be easily formed or segregated after formation to relatively narrow size tolerances. Size can be measured by FSC, thus size may serve as a code. Granularity may also be introduced into carriers, for example, by varying the amount of a reflective particles suspended within the carrier, or by degree of cross linking used to make the carrier. Fluorescence may be imparted by adding a blend of fluorophores, or by adding discretely fluorescent particles. Such particles may also contribute to the granularity of the carrier for SSC interrogation.

Two-dimensional arrays, such as when carriers are dispersed on a surface of a slide, may be interrogated by a wide variety of methods. Individual carriers may be interrogated by using a microscopy objective to view each particular carrier, observing the code, target-compound interaction, or both. Alternatively, a CCD camera may observe the entire array simultaneously using pixels to delineate each carrier. Once active carriers are identified, the CCD camera may then focus in with another microscopy objective lens, to "see" the code on a particular carrier. If the array has been predetermined, perhaps by the manufacturer as discussed above, then the CCD need only identify active carriers and the carrier identity revealed later by correlation of the CCD pixel coordinate with the carrier code of corresponding to that pixel coordinate. This assumes that an alignment means exists between the predetermined array and the CCD pixel array. Two dimensional array illumination may be either epi-illumination or transillumination. Autofluorescence may also be used as well as autoillumination such as with bioluminescent systems well known in the art.

Other physical means may be used to interrogate carriers either for target-compound interactions or carrier codes. For example, molecular recognition may be exploited not only to impart an optical character to a carrier, but also physical character as well. Agglutination may be used to separate carriers by introducing other particles or molecular structures that will cause like carriers to combine such that they may be separated from uncombined carriers. Carriers may be selectively absorbed onto surfaces by attaching molecular recognition elements to a surface, and exposing carriers to such surface, thereby causing such carriers to absorb to the surface.

EXAMPLES

Example 1

Taggants as Carriers

Two complementary 50-mer oligonucleotides, 1S (sense) and 1A (anti-sense), were covalently attached to two different classes of taggants taggants S and taggants A respectively. A CY3 labeled, single-strand DNA, p53s (sense strand) approximately 300 nucleotides in length and produced in a PCR reaction and used as the test DNA. This test DNA is complementary to oligonucleotide 1S and therefore expected to hybridize to it to a much greater extent than to strand 1A.

Following the hybridization reaction, a high amount of fluorescence was present on taggants S (containing the 1S, sense strand) and a negligible amount of fluorescence was observed on taggants A (containing the strand 1A, anti-sense strand). The difference in signal between taggants S and A represents specific hybridization. The experiments prove the following:

DNA can be linked to taggant carriers.

DNA can react as predicted when linked to taggant carriers. The hybridization reaction is specific and it can be quantified.

The carrier class to which the compound is attached can identify the reaction product.

Example 2

Molecular Beacons

Molecular beacons can be immobilized on the encoded carriers by following the method described by Fang. To accomplish this the carriers can be treated with avidine (0.1% solution in PBS) followed by a cross-linking treatment with a 1% glutaraldehyde solution for one hour. After washing with a 1M Tris/HCl buffer the coated carriers are mixed with the biotinylated beacons (at a concentration of $1\times10^{-6}$ M) for 10 minutes. Lastly the beacons are washed with PBS and are used in the hybridization reaction.

We claim:

1. A system for conducting a multiplexed experiment comprising a mixture of microcarriers including multiple classes of microcarriers, each microcarriers having a code, at least one flat viewing surface and a shape that self-orients the viewing surface to face a viewing direction, a first class of microcarriers in the mixture, each microcarriers in the first class having a first code configuration characterized by a first optically distinguishable combination of colored spatial indicia formed from a flat ribbon of parallel-fused glass fibers including at least one transparent fiber, a second class of microcarriers in the mixture, each microcarrier in the second class having a second code configuration characterized by a second optically distinguishable combination of colored spatial indicia formed from a flat ribbon of parallel-fused glass fibers including at least one transparent fiber, and biological cells attached to at least some of the microcarriers, wherein the code on a microcarriers identifies a characteristic of a cell carried by the microcarriers.

2. The system of claim 1, wherein the mixture of microcarriers includes at least three classes of microcarriers, each class of microcarriers having a distinctive code configuration.

3. A system for conducting a multi-plexed experiment comprising a mixture of microcarriers including multiple classes of microcarriers, each microcarriers having a code, at least one flat viewing surface and a shape that self-orients the viewing surface to face a viewing direction, a first class of microcarriers in the mixture each microcarriers in the first class having a first code configuration characterized by a first optically distinguishable combination of colored fibers and at least one transparent fiber, a second class of microcarriers in the mixture each microcarriers in the second class having a second code configuration characterized by a second optically distinguishable combination of colored fibers and at least one transparent fiber, and biological cells attached to at least some of the microcarriers, wherein the code on a microcarrier identifies a characteristic of a cell carried by the microcarriers.

4. The system of claim 3, wherein the fibers in each microcarriers are fused together.

5. The system of claim 3, wherein the fibers are glass.

6. The system of claim 3, wherein the fibers are plastic.

7. The system of claim 3, wherein the mixture of microcarriers includes at least three classes of microcarriers, each class of microcarrier having a distinctive code configuration.

8. The system of claim 3, wherein the microcarriers are formed from a flat ribbon of parallel fused colored fibers.

9. A system for conducting a multiplexed experiment comprising a mixture of microcarriers including multiple classes of microcarriers, a first class of microcarriers in the mixture, each microcarriers in the first class having a first optically detectable code and at least one transparent portion, a second class of microcarriers in the mixture, each microcarriers in the second class having a second optically detectable code and at least one transparent portion, wherein each microcarriers has at least one flat viewing surface and a shape that self-orients the viewing surface to face a viewing direction, and biological cells attached to at least some of the microcarriers, wherein the code on a microcarriers identifies a characteristic of a cell carried by the microcarriers.

10. The system of claim 9, wherein each microcarriers is at least partially formed by a combination of differently-colored fibers, the combination of differently color fibers defining the code.

11. The system of claim 10, wherein the fibers in each microcarriers are fused together.

12. The system of claim 10, wherein the fibers in each microcarriers comprise glass.

13. The system of claim 10, wherein the fibers in each microcarriers ceomprise plastic.

14. The system of claim 9, wherein each microcarriers is formed from a flat ribbon of parallel fused colored fibers.

15. The system of claim 1, wherein microcarriers from the first and second classes are randomly distributed on a surface for analysis.

16. The system of claim 1, wherein the cells are attached to microcarriers via antibodies that bind specifically to antigens displayed on the cells.

17. The system of claim 3, wherein microcarriers from the first and second classes are randomly distributed on a surface for analysis.

18. The system of claim 9, microcarriers from the first and second classes are randomly distributed on a surface for analysis.

* * * * *